(12) United States Patent
Morris et al.

(10) Patent No.: US 8,031,925 B2
(45) Date of Patent: Oct. 4, 2011

(54) METHOD AND COMPUTER-PROGRAM PRODUCT FOR DETECTING AND QUANTIFYING PROTEIN SPOTS

(75) Inventors: Jeffrey S. Morris, Pearland, TX (US); Howard Gutstein, Bellaire, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 940 days.

(21) Appl. No.: 11/971,041

(22) Filed: Jan. 8, 2008

(65) Prior Publication Data
US 2008/0166030 A1    Jul. 10, 2008

Related U.S. Application Data

(60) Provisional application No. 60/884,141, filed on Jan. 9, 2007.

(51) Int. Cl.
*G06K 9/00* (2006.01)
*G01N 33/48* (2006.01)

(52) U.S. Cl. .................... 382/128; 382/274; 702/19

(58) Field of Classification Search ................ 382/100, 382/128, 129, 130, 131, 132, 133, 134, 154, 382/168, 173, 181, 194, 199, 232, 254, 274, 382/276, 285, 312; 705/2; 204/601, 616; 356/328; 702/19
See application file for complete search history.

(56) References Cited

U.S. PATENT DOCUMENTS

| | | | | |
|---|---|---|---|---|
| 4,351,611 A | * | 9/1982 | Leif | 356/328 |
| 4,624,768 A | * | 11/1986 | Yoshida et al. | 204/616 |
| 5,073,963 A | * | 12/1991 | Sammons et al. | 382/128 |
| 6,061,657 A | * | 5/2000 | Whiting-O'Keefe | 705/2 |
| 6,485,625 B1 | * | 11/2002 | Simpson et al. | 204/601 |
| 6,611,766 B1 | * | 8/2003 | Larsen et al. | 702/19 |

OTHER PUBLICATIONS

Almeida, J.S., Stanislaus, R., Krug, E. and Arthur, J.M., "Normalization and Analysis of Residual Variation in Two-Dimensional Gel Electrophoresis for Quantitative Differential Proteomics." in: Proteomics (2005), pp. 5 and 1242-1249.

Anderson, L. and Seilhammer, J., "A Comparison of Selected mRNA and Protein Abundances in Human Liver." in: Electrophoresis (1997), pp. 18 and 533-537.

Champion, K.M., Nishihara, J.C., Joly, J.C. and Amott, D., "Similarity of the *Escherichia coli* Proteome Upon Completion of Different Biopharmaceutical Fermentation Processes." in: Proteomics (2005), pp. 1 and 1133-1148.

Coombes, K.R., Tsavachidid, S., Morris, J.S., Baggerly, K.A., and Kuerer, H.M., "Improved Peak Detection and Quantification of Mass Spectrometry Data Acquired From Surface-Enhanced Laser Desorption and Ionization by Denoising Spectra With the Undecimated Discrete Wavelet Transform." in: Proteomics (2005), pp. 5 and 4107-4117.

(Continued)

*Primary Examiner* — Seyed Azarian
(74) *Attorney, Agent, or Firm* — Sheppard, Mullin, Richter & Hampton LLP; David E. Heisey

(57) ABSTRACT

The present inventions is directed to a method and computer program product for detecting and quantifying protein spots, including: generating an average gel image by taking a pixel-by-pixel average of the intensities of a plurality of aligned gel images; detecting spots on the average gel image using pinnacle detection; and quantifying spots on individual gels using the maximum intensity within fixed neighborhoods surrounding pinnacle locations found in the average gel image.

15 Claims, 4 Drawing Sheets

OTHER PUBLICATIONS

Cuello, A.C., Carson, S., Brain Microdissection Techniques. New York, John Wiley and Sons. 2003. p. 37-116.

Cutler, P., Heald, G., Wite, I.R., and Roan, J., "A Novel Approach to Spot Detection for Two-Dimensional Gel Electrophoresis Images Using Pixel Value Collection." in: Proteomics (2003), pp. 3 and 392-401.

Donoho, D. and Johnstone, I.M., "Ideal Spatial Adaptivation Via Wavelet Shrinkage." in: Biometrika (1994), pp. 81 and 425-455.

Gygi, S.P., Rochon, Y., Franza, B.R. and Aebersold, R., "Correlation Between Protein and mRNA Abundance in Yeast." in: Mol. Cell Biol., (1999), pp. 1720-1730.

Klose, F., "Protein Mapping by Combined Isoelectric Focusing and Electrophoresis of Mouse Tissues. A Novel Approach to Testing for Induced Point Mutations in Mammals." in: Humangenetik (1975). pp. 26, 231-243.

Mahon, P. and Dupree, P., "Quantitative and Reproducible Two-Dimensional Gel Analysis Using Phoretix 2D Full." in: Electrophoresis (2001), pp. 22, 2075-2085.

Morris, J.S., Coombes, K.R., Koomen, J., Baggerly, K.A. and Kobayashi, R., "Feature Extraction and Quantification for Mass Spectrometry in Biomedical Applications Using the Mean Spectrum." in: Bioinfomatics (2005), pp. 21, 1764-1775.

Nishihara, J.C. and Champion, K.M., "Quantitative Evaluation of Proteins in One and Two-Dimensional Polyacrylamide Gels Using a Fluorescent Stain." in: Electrophoresis (2002), pp. 23, 2203-2215.

O'Farrell, P.H., "High Resolution Two-Dimensional Electrophoresis of Proteins." in: J Biol Chem (1975), pp. 250, 4007-4021.

Storey, J.D., "The Positive False Recovery Rate: A Bayesian Interpretation and the Q-Value." in: The Annals of Statistics (2003), pp. 31(6), 2013-2035.

Xu, It, Walla, B.C., Diaz, M.F., Fuller, G.N., and Gutsein, H.B., "Intermittent Lumbar Puncture in Rats: A Novel Method for the Experimental Study of Opiod Tolerance." in: Anesth Analg (2006), pp. 103, 714-720.

Risk Glossary, http://www.riskglossary.com/link/capital_asset_pricing_model.htm.

Wikipedia, http://en.wikipedia.org/wiki/Modern_portfolio_theory.com.

Finch, S., "Royalty Rates: Current Issues and Trends.", in: Journal of Commerical Biotechnology, vol. 7, Winter 2001.

Webster, J., and Philippon, T., "Valuation of Biotechnology Companies and Their Assets-Probability Effected Discounted Cash Flows." in: Les Nouvelles, (Dec. 2004), pp. 167.

Johnston, D., International Petroleum Fiscal Systems and Production Sharing Contracts. PennWell Publishing Company, pp. 138.

Wavelet Toolbox (RWT), http://www.dsp-rice.edu/software/rwt.shtml.

* cited by examiner

Initial Instruction Set adapted to direct the data processor to receive data representative of the plurality of two-dimensional gel electrophoresis images.

Instruction set #1 adapted to direct the data processor to generate average gel image by taking a pixel-by-pixel average of the intensities of the individual gel images, as aligned to one another.

Instruction set #2 adapted to direct the data processor to detect spots on the average gel image by detecting pinnacles, each detected spot of the average gel image having a corresponding pinnacle and pinnacle location.

Instruction set #3 adapted to direct the data processor to quantify spots on one or more individual gel images using maximum intensities within fixed neighborhoods surrounding pinnacle locations found in the average gel image.

COMPUTER-READABLE MEDIUM

FIG. 4

Initial Instruction Set adapted to direct the data processor to receive data representative of the plurality of two-dimensional gel electrophoresis images.

Instruction Set #1 adapted to direct the data processor to subtract the global minimum pixel intensity of each individual gel image from every pixel intensity of the gel image.

Instruction Set #2 adapted to direct the data processor to generate an average gel image by taking a pixel-by-pixel average of the intensities of the individual gel images, as aligned to one another, and as previous processed by Instruction Set #1.

Instruction Set #3 adapted to direct the data processor to generate wavelet coefficients of a discrete wavelet transformation for the average gel image given a particular choice of wavelet basis.

Instruction Set #4 adapted to direct the data processor to apply hard thresholding to the wavelet coefficients by setting all coefficients that are below a threshold $\phi=\delta\sigma$ to 0 while leaving all coefficients $\geq \phi$ unaffected.

Instruction Set #5 adapted to direct the data processor to generating a de-noised average image by applying an inverse discrete wavelet transform to the threshold wavelet coefficients.

Instruction Set #6 adapted to direct the data processor to detect spots on the de-noised average gel image by detecting pinnacles, a pinnacle being detected as pixel location whose intensity is a local maximum in both the horizontal and vertical directions on the average gel image, and whose intensity is greater than a certain threshold, by default the $75^{th}$ percentile intensity value of the average gel image.

Instruction Set #7 adapted to direct the data processor to combine pinnacles that are within a certain proximity to one another (by default +/- 2 pixels), keeping the one with the highest intensity.

Instruction Set #8 adapted to direct the data processor to quantify each spot on the gel by the maximum intensity within a square, but default the 5 × 5 pixel square formed by taking the corresponding pinnacle location in the average gel and extending out +/- 2 pixels in the horizontal and vertical directions.

COMPUTER-READABLE MEDIUM

FIG. 5

METHOD AND COMPUTER-PROGRAM PRODUCT FOR DETECTING AND QUANTIFYING PROTEIN SPOTS

REFERENCE TO RELATED APPLICATIONS

This application claims priority to U.S. Provisional Patent Application No. 60/884,141, filed Jan. 9, 2007, the content of which is incorporated herein by reference in its entirety.

GOVERNMENT INTEREST

This invention was made with government support under CA107304, DA018310, and DA015146, awarded by The National Institutes of Health. The government has certain rights in the invention.

FIELD OF THE INVENTION

The present invention is generally directed to a method and computer program product for detecting and quantifying protein spots, and more particularly to detecting and quantifying such spots in 2-dimensional gel electrophoresis data or other 2-dimensional proteomic technologies.

BACKGROUND OF THE INVENTION

Proteomics is capable of generating new hypotheses about the mechanisms underlying physiological changes. The perceived advantage of proteomics over gene-based global profiling approaches is that proteins are the most common effector molecules in cells. Changes in gene expression may not be reflected by changes in protein expression. See, Anderson, L. & Seilhammer, J. A. A comparison of selected mRNA and protein abundances in human liver. *Electrophoresis* 18, 533-537 (1997). See also, Gygi, S. P., Rochon, Y., Franza, B. R. & Aebersold, R. Correlation between protein and mRNA abundance in yeast. *Mol. Cell Biol.* 19, 1720-1730 (1999). However, the large number of amino acids and post-translational modifications make the complexity inherent in analyzing proteomics data greater than for genomics data.

Several methods have been developed for separating proteins extracted from cells for identification and analysis of differential expression. One of the most widely used is 2-dimensional gel electrophoresis (2DE). See Klose, J. Protein mapping by combined isoelectric focusing and electrophoresis of mouse tissues. A novel approach to testing for induced point mutations in mammals. *Humangenetik* 26, 231-243 (1975). See also, O'Farrell, P. H. High resolution two-dimensional electrophoresis of proteins. *J. Biol Chem* 250, 4007-4021 (1975). In this method, proteins are first separated in one direction by their isoelectric points, and then in a perpendicular direction by molecular weight. As 2DE-based proteomic studies have become more complex, one of the major challenges has been to develop efficient and effective methods for detecting, matching, and quantifying spots on large numbers of gel images. These steps extract the rich information contained in the gels, so are crucial to perform accurately if one is to make valid discoveries.

In current practice, the most commonly used spot detection and quantification approach involves three steps. First, a spot detection method is applied to each individual gel image to find all protein spots and draw their boundaries. Second, spots detected on individual gel images are matched to a master list of spots on a chosen reference gel image, requiring specification of vertical and horizontal tolerances since spots on different gel images are rarely perfectly aligned with one another. Third, "volumes" are computed for each spot on each gel image by summing all pixel values within the defined spot regions.

Unfortunately, these methods lack robustness. Errors are frequent and especially problematic for studies involving large numbers of gels. The errors consist of three main types, spot detection, spot matching, and spot boundary estimation errors. Detection errors include merging two spots into one, splitting a single spot into two, not detecting a spot, and mistaking artifacts for spots. Also, automatically detected spot boundaries can be inaccurate, increasing the variability of spot volume calculations. Matching errors occur when spots on different gel images are matched together but do not correspond to the same protein. These errors are pervasive and can obscure the identification of differential protein expression. Almeida, et al. list mismatched spots as one of the major sources of variability in 2DE, and Cutler, et al. identify the subjective nature of the editing required to correct these errors as a major problem. Almeida, J. S., Stanislaus, R., Krug, E. & Arthur, J. M. Normalization and analysis of residual variation in two-dimensional electrophoresis for quantitative differential proteomics. *Proteomics* 5, 1242-1249 (2005); Cutler, P., Heald, G., White, I. R. & Ruan, J. A novel approach to spot detection for two-dimensional gel electrophoresis images using pixel value collection. *Proteomics* 3, 392-401 (2003). Extensive hand editing is needed to correct these various errors and can be very time-consuming, taking 1 to 4 hours per gel image. Id. Taken together, these factors limit throughput and bring the objectivity and reproducibility of results into question. Also, one must decide what to do about missing values caused by spots that are matched across some, but not all gel images. A number of ad hoc strategies have been employed, but all have weaknesses and bias quantifications.

SUMMARY OF THE INVENTION

The present invention is directed to a method and computer-program product for detecting and quantifying protein spots. It is more specifically directed to detecting and quantifying such spots in 2-dimensional gel electrophoresis data or other 2-dimensional proteomic technologies (e.g., LC-MS).

In an exemplary method, the present invention provides a method of detecting and quantifying protein spots in 2-dimensional gel electrophoresis data, where the data comprises a plurality of individual gel images that have been previously aligned to one another. The method involves: generating an average gel image by taking a pixel-by-pixel average of the images of the individual gels images; detecting spots on the average gel image using pinnacle detection; and, quantifying spots on individual gel images using the maximum intensity within fixed neighborhoods surrounding pinnacle locations found in the average gel image.

In an exemplary computer program product, the present invention provides a product for directing a computer processor to detect and quantify protein spots in a plurality of two-dimensional gel electrophoresis images that have been aligned to one another (such alignment may be done by way of the superimposition of corresponding gel features across gels). Each individual gel image has a two-dimensional array of pixels, each of which has an intensity. The computer program product includes: a computer readable medium; an initial set of instructions embodied on the computer readable medium adapted to direct the data processor to receive data representative of the plurality of two-dimensional gel electrophoresis images; a first set of instructions embodied on the computer readable medium adapted to direct the data processor to generate an average gel image by taking a pixel-by-pixel average of the intensities of the individual gel images, as aligned to one another; a second set of instructions embodied on the computer readable medium adapted to direct the data processor to detect spots on the average gel by detecting pinnacles, each detected spot of the average gel image having a corresponding pinnacle and pinnacle location; a third set of instructions embodied on the computer readable medium adapted to direct the data processor to quantify spots on one or more of the individual gel images using maximum intensity within fixed neighborhoods surrounding the pinnacle locations found in the average gel.

In a computer program, the present invention provides a program to be installed in a computer for controlling the computer to perform the process for detecting and quantifying protein spots in 2-dimensional gel electrophoresis data. The process involves: receiving data related to superimposition of corresponding gel features across gels; generating an average gel by taking a pixel-by-pixel average of aligned gel intensities; detecting spots on the average gel by applying a wavelet-based de-noising filter and then detecting pinnacles; quantifying spots on each individual gel using the maximum intensity within fixed neighborhoods surrounding the pinnacle locations found in the average gel.

Other features and aspects of the invention will become apparent from the following detailed description, taken in conjunction with the accompanying drawings, which illustrate, by way of example, the features in accordance with embodiments of the invention. The summary is not intended to limit the scope of the invention, which is defined solely by the claims attached hereto.

BRIEF DESCRIPTION OF THE DRAWINGS

The present invention, in accordance with one or more various embodiments, is described in detail with reference to the following figures. The drawings are provided for purposes of illustration only and merely depict typical or example embodiments of the invention. These drawings are provided to facilitate the reader's understanding of the invention and shall not be considered limiting of the breadth, scope, or applicability of the invention. It should be noted that for clarity and ease of illustration these drawings are not necessarily made to scale.

Some of the figures included herein illustrate various embodiments of the invention from different viewing angles. Although the accompanying descriptive text may refer to such views as "top," "bottom" or "side" views, such references are merely descriptive and do not imply or require that the invention be implemented or used in a particular spatial orientation unless explicitly stated otherwise.

These and other features and advantages of the various embodiments disclosed herein will be better understood with respect to the following description and drawings, in which like numbers refer to like parts throughout, and in which:

FIG. 1 illustrates a basic exemplary system for implementing exemplary steps of the present method and instruction sets of the present computer program product.

FIG. 2 illustrates a first exemplary method according to the present invention in terms of a flow diagram.

FIG. 3 illustrates a second exemplary method according to the present invention in terms of a flow diagram.

FIG. 4 illustrates a first exemplary computer-program product according to the present invention.

FIG. 5 illustrates a second exemplary computer-program product according to present invention.

DETAILED DESCRIPTION OF THE INVENTION

In the following paragraphs, the present invention will be described in detail by way of example with reference to the attached drawings. Throughout this description, the preferred embodiment and examples shown should be considered as exemplars, rather than as limitations on the present invention. As used herein, the "present invention" refers to any one of the embodiments of the invention described herein, and any equivalents. Furthermore, reference to various feature(s) of the "present invention" throughout this document does not mean that all claimed embodiments or methods must include the referenced feature(s).

The present invention is directed to a method and a computer program product for detecting and quantifying protein spots. It is more specifically directed to detecting and quantifying such spots in 2-dimensional gel electrophoresis data or other 2-dimensional proteomic technologies (e.g., LC-MS). With respect to 2-dimensional gel electrophoresis data, the method is used with individual gel images that have undergone image alignment ("aligned gel images"), defined as the superimposition of corresponding gel features across gel images. Gel images are typically aligned using the commercially available TT900 alignment program (Nonlinear Dynamics), although one may use any suitable program.

Figure 1:
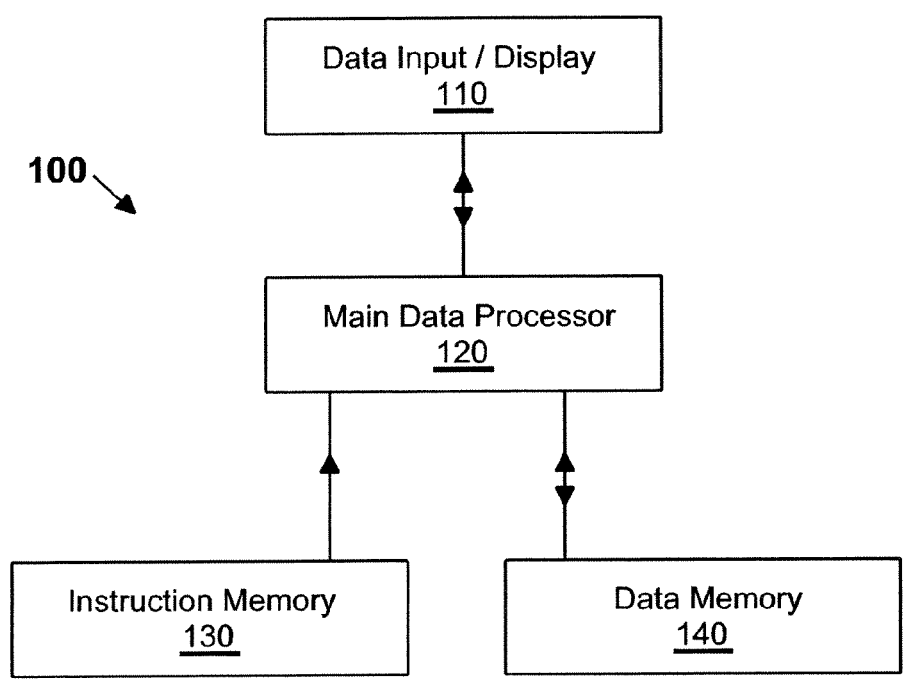

FIG. 1 shows an exemplary data processing system 100 for implementing the method of the invention. In particular, system 100 comprises: data input/display 110 for interfacing with a human user or system that supplies or desires to obtain data regarding protein spots on 2-dimensional gel images; main processor 120; instruction memory 130 and data memory 140 for the main processor. Memories 130 and 140 may be separate or different sections of the same memory bank. The main processor may be configured to implement the method of the present invention by the instructions stored or loaded in instruction memory 130.

Figure 2:
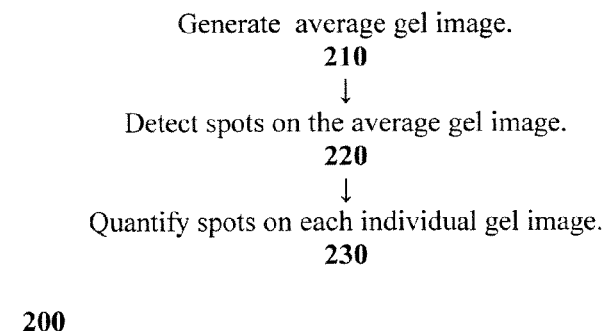

A first exemplary method 200 of the invention is generally described in relation to FIG. 2. After image alignment, an average gel image is generated in step 210 by taking a pixel-by-pixel average of the intensities of the aligned gel images. By default, the arithmetic mean is taken, although other generalized means could be used as well, including the geometric mean, harmonic mean, or a certain quantile. Spots are detected on the average gel image in step 220 using pinnacle detection. Spot detection detecting pinnacles, or pixels that are local maxima in both the vertical and horizontal directions with intensities above a specific threshold (FIG. 1). As an option, the average gel image may be processed to reduce noise in the image (i.e., "de-noising" the image) before detecting the pinnacles. Using the average gel image for spot detection yields greater sensitivity and specificity, since real protein spots are reinforced across gel images, while noise and artifacts specific to individual gel images tend to average out.

With further reference to FIG. 2, spots on each individual gel image are quantified in step 230 using the maximum intensity within fixed neighborhoods surrounding the pinnacle locations found in the average gel image. More specifically, the locations of pinnacles found on the average gel image are identified on each of the individual gel images, neighborhoods around the corresponding pinnacle locations are then identified on the individual gel image (not the average gel image), a neighborhood being a two-dimensional set of pixels, and the maximum intensity is detected within each neighborhood. Quantifying spots using maximum intensity within fixed neighborhoods is quicker and easier than computing spot volumes since there is no need to determine spot boundaries, a difficult and potentially error-prone process. Also, there are typically no missing values in the datasets since the pinnacle-based intensity value is well-defined for all gel images in a set.

Figure 3:
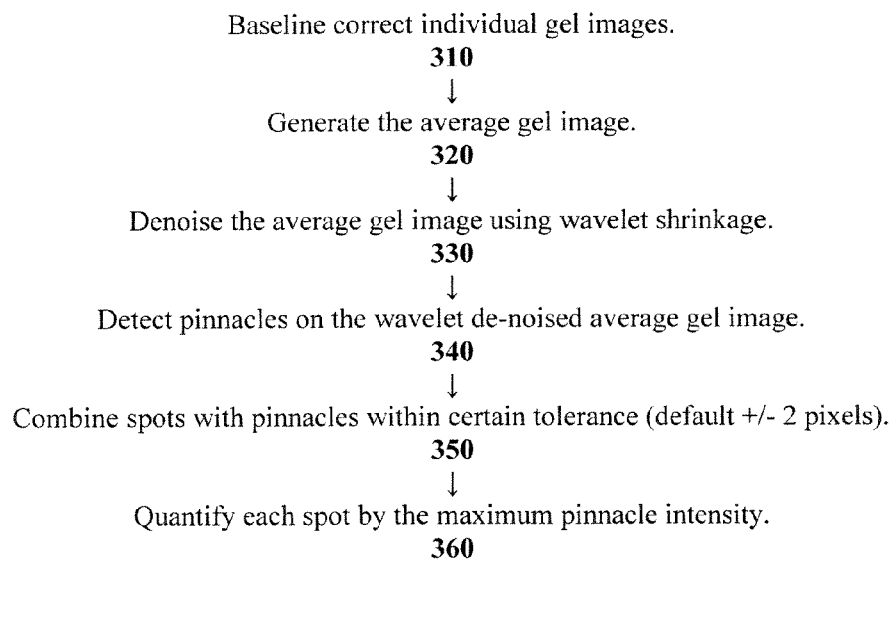

A second exemplary method 300 is generally described in relation to FIG. 3. Preferably after image alignment, each individual gel image is baseline corrected in step 310. This is typically done by subtracting the global minimum pixel intensity of the gel image from every pixel intensity value of the gel image. Alternatively, the baseline correction could be done before the image alignment process; it makes no practical difference on the results. Subsequently, the average gel is generated in step 320. This is done by averaging the baseline-corrected intensity pixel-by-pixel across all gel images in the experiment. Then, the average gel image can be de-noised (i.e., processed to reduce noise) using wavelet shrinkage in step 330. Other de-noising filters could also be used, but wavelets have been shown to perform exceptionally well in the context of de-noising.

De-noising may be performed as follows. First, given a particular choice of wavelet basis and level of decomposition, wavelet coefficients of a two-dimensional discrete wavelet transformation (2-D DWT) are computed for the average gel image (an undecimated DWT, abbreviated as UDWT, is preferably used, and other alternatives such as complex wavelets can also be used, if desired). Second, hard thresholding is applied to the wavelet coefficients. Here, the term hard thresholding has the accepted meaning in the wavelet de-noising context, and involves truncating coefficient values to zero when the magnitudes of the values are less than a predetermined threshold value, while leaving coefficients whose magnitude is greater than the threshold unaffected. Third, the de-noised average gel image is generated (i.e., the de-noised signal is reconstructed) by applying the inverse transform of the 2-D DWT to the thresholded wavelet coefficients (the inverse UDWT is use if the UDWT was used in the first step). The mathematical equations and processing for implementing the above first and third steps can be found in any tutorial on wavelet transforms, and a detailed explanation in not needed here to enable one of ordinary skill in the art to make and use the present invention without undue experimentation. One inventive aspect of the above three steps is the application of hard thresholding to the wavelet coefficients between the first and third steps.

With further reference to FIG. 3, pinnacles are detected on the de-noised average gel image in step 340. A pixel location is said to contain a pinnacle if its intensity is a local maximum in both the horizontal and vertical directions on the gel image (i.e., in two orthogonal directions on the gel image), and if its intensity is greater than some predetermined threshold (e.g., the $75^{th}$ percentile of all intensities on the gel image, although this setting is adjustable and other alternatives could be used). Any pinnacles located within a predetermined proximity of each other are combined in step 350 (e.g., within +/−2 pixels, although again this setting is adjustable and other alternatives could be used). Each spot is quantified by the maximum pinnacle intensity in step 360.

The method of detecting and quantifying protein spots may be implemented by one or more computer program products comprising machine readable or interpretable instructions for directing a data processing system, such as a microcomputer, to perform the steps of the exemplary methods. Each computer program product comprises a computer-readable medium, such for example as ROM, RAM, magnetic tape, magnetic disk, carrier waves (such as for internet downloading), etc., and a plurality of sets of instructions embodied on the computer-readable medium, each set directing a data processing system to execute a respective step of the method being implemented.

FIG. 4 illustrates a first exemplary computer-program product having a listing of instructions sets for implementing the above-described first exemplary method. FIG. 5 depicts a second exemplary computer-program product having a listing of instruction sets for implementing the above-described second exemplary method. In view of the listings of the instruction sets and the description of the present invention herein, it is well within the ability of one of ordinary skill in the art to construct the instruction sets shown in FIGS. 4 and 5 in any desired programming language, including scripting languages, without undue experimentation.

The method of the present invention was compared with current versions of the commercial software packages Progenesis and PDQuest in detecting, matching, and quantifying protein spots using two dilution series. The first was created by Nishihara and Champion; the inventors prepared the second. Nishihara, J. C. & Champion, K. M. Quantitative evaluation of proteins in one- and two-dimensional polyacrylamide gels using a fluorescent stain. *Electrophoresis* 23, 2203-2215 (2002). The percentage of spots correctly matched by the automatic algorithms was summarized. Reliability of spot quantifications was assessed by measuring the strength of linear association ($R^2$) between the spot quantifications and the protein loads in the dilution series for each detected spot. Precision was assessed using the coefficient of variation (% CV) of spots within the different dilution groups. All comparisons were based on results generated solely by the three algorithms, without any subsequent editing.

For the Nishihara and Champion study, the method of the present invention detected 1380 spots, which by definition were found and quantified in all gels. PDQuest detected 2692 spots of which 745 were "unratched spots" found on only one gel. An additional 571 spots were detected on more than one gel, but were not included in the analyses because they were not found on 3 out of 4 gels for at least one group, the same exclusion criterion used by Nishihara and Champion. The match percentage of the 1376 spots found on ¾ gels in at least one group was 60%.

Progenesis detected 1986 unique spots, of which 990 were unmatched and 121 were not found on ¾ gels in at least one group. The match percentage of the 875 spots found on ¾ gels for at least one group was 84%. If attention is restricted only to those spots that had no missing values on any gel, as with the method of the present invention, one would have been left with only 377 and 271 spots for PDQuest and Progenesis, respectively.

The top half of Table 1 contains reliability results. The method of the present invention yielded more reliable spot quantifications over this dilution series (mean $R^2$=0.931) than either PDQuest (0.835) or Progenesis (0.883). The present method found many more reliable spots (defined as $R^2$>0.90) than either PDQuest or Progenesis (1146 vs. 847 or 666, respectively). Table 2 shows that the present method also generated more consistent quantifications within the 30 μg protein load group. The present method generated a lower CV (mean 18.1) than either PDQuest (54.7) or Progenesis (40.3), and found far more spots with CV<20% (902 vs. 498 and 304, respectively).

To determine whether the method of the present invention performed better than the other methods only because the gels were pre-aligned, PDQuest and Progenesis were also run on the set of aligned gels. In general, alignment tended to slightly improve the reliability, but not to the levels of the present invention (Table 1). Alignment had inconsistent effects on match percentage, and decreased measurement precision for both PDQuest and Progenesis (Table 2).

A dilution series created from SH-SY5Y neuroblastoma cell extracts (Tables 1 and 2, last rows) was also analyzed. The present method detected 1013 spots, while PDQuest identified 1297 spots that were found on ⅔ gels in at least one group, with a match percentage of 45%. Progenesis detected 979 spots on ⅔ gels in at least one group with a match percentage of 30%. The present method also yielded more reliable spot quantifications over this dilution series (mean $R^2=0.905$) than either PDQuest (0.735) or Progenesis (0.662).

The method of the present invention also found many more reliable spots (663) than either PDQuest (406) or Progenesis (295). Again, the present method generated more consistent measurements (mean CV in 50 µg load group 12.2) than either PDQuest (64.4) or Progenesis (53.2), and found far more spots with CV<20% (859 vs. 267 and 188, respectively). Again, the alignment had inconsistent effects on the performance of PDQuest and Progenesis. Reliability and match percentage improved for both methods, but was still far inferior to the present method (Table 1). Precision improved for PDQuest but worsened for Progenesis (Table 2).

Experimental Methods: Description of Experiments

Nishihara and Champion Dilution Series

Nishihara and Champion prepared a dilution series experiment using a sample of *E. coli* with seven different 2D gel protein loads spanning a 100-fold range (0.5, 7.5, 10, 15, 30, 40, and 50 µg). Four gels were run at each protein load. Details of the conduct of the 2DE are described in Champion, et al., and the details of the staining and image capture procedures are described in Nishihara and Champion. Champion, K. M., Nishihara, J. C., Joly, J. C. & Arnott, D. Similarity of the *Escherichia coli* proteome upon completion of different biopharmaceutical fermentation processes. *Proteomics* 1, 1133-1148 (2001); Nishihara, J. C. & Champion, K. M. Quantitative evaluation of proteins in one- and two-dimensional polyacrylamide gels using a fluorescent stain. *Electrophoresis* 23, 2203-2215 (2002). el images were provided the inventors courtesy of Dr. Kathleen Champion-Francissen, Genentech, and were used to compare the method of the present invention with PDQuest and Progenesis. Nishihara and Chanpion previously used this series to evaluate the performance of several 2D analysis packages by analyzing 20 corresponding spots from all the gels. By only investigating 20 spots, however, they did not gain an accurate picture of the methods' performance in detecting, matching, and quantifying spots across the entire gel. Therefore, analysis methods using all spots detected in this dilution series were evaluated. Progenesis and PDQuest results for the 20 selected spots were comparable to the results previously obtained by Nishihara and Champion (data not shown).

SH-SY5Y Neuroblastoma Cell Dilution Series

SH-SY5Y cells were grown to 60-70% confluence and then harvested. Cells were then re-suspended using the ProteoPrep™ (Sigma) total extraction kit and the suspension ultrasonicated on ice for 15 sec. bursts at 70% amplitude for a total time of 1 min. After sonication, the suspension was centrifuged at 15,000×g for 30 min. at 15° C. The samples were then reduced for 1 h at RT by adding tributylphosphine to a final concentration of 5 mM and alkylated in the dark for 1.5 h at RT by adding iodoacetamide to a final concentration of 15 mM. 11 cm IPG strips (Bio-Rad) were then re-hydrated in 100 µl of sample buffer for 2 h at RT. Protein samples were then applied to the strips in 150 µl of buffer and IPGs were then focused for 100 kVh. Voltage was increased from 0 to 3000 V over 5 h (slow ramp), 3-10,000 V over 3 h (linear ramp), followed by additional hours at 10,000 V. IPGs were then equilibrated in SDS-equilibration buffer containing 3M urea, 2.5% (w/v) SDS, 50 mM Tris/acetate buffer (pH 7.0), and 0.01% (w/v) bromophenol blue as a tracking dye for 20 min. The equilibrated strips were then placed on 8-16% polyacrylamide gels (Bio-Rad) and proteins separated by size. Run conditions were 50 mA/gel until the bromophenol blue reached the end of the gel. Proteins were visualized using SYPRO ruby stain (Bio-Rad). Gels were fixed for 30 min. in a solution containing 10% methanol and 7% acetic acid. After fixation, gels were stained in 50 ml of SYPRO ruby overnight in the dark. Prior to imaging, gels were de-stained in 10% methanol and 7% acetic acid for 2 h. Gels were imaged using a Kodak Image Station 2000R. Gel images were subsequently cropped to exclude edge artifacts and streaks. The same cropped image area was used for all analytical protocols.

Experimental Methods: Description of Analytical Methods

All gels used in these studies were processed and analyzed using three different methods: Progenesis PG240 version 2006 (Nonlinear Dynamics Ltd., Newcastle-upon-Tyne, UK), PDQuest Version 8.0 (Bio-Rad Laboratories, Hercules, Calif., USA), and the method of the present invention. The present method was applied to images that were first aligned using the TT900 software program (Nonlinear Dynamics), and involved average gel computation, pinnacle detection, and pinnacle-based quantification using computer code written in MATLAB (version R2006a, The MathWorks, Inc.) using Windows XP-based PCs. Specific analysis steps are detailed below.

Progenesis

Gels were processed using the Analysis Wizard, which is a stepwise approach for selecting preprocessing options. Gels were grouped by protein load, and the same gel was selected as the top reference gel for both the aligned and unaligned image sets. Background subtraction was performed using the Progenesis Background method. Combined warping and matching was selected for the unaligned images, and property-based matching was selected for the aligned images, as recommended by the manufacturer. Normalization was not done, since this would eliminate the linearity of quantifications with protein load used to evaluate reliability. The minimum spot area was set to 1, and the split factor set at 9. These settings produced a similar number of spots to that reported by Nishihara and Champion using an earlier version of this program. No manual editing of the data was performed. The data were simply exported to Excel and spots present in 3 of 4 replicates in the Nishihara and Champion series, or 3 of 3 replicates in the SH-SY5Y dilution series determined.

PDQuest

Gels were processed using the Spot Detection Wizard. Gels were grouped by protein load, default background subtraction and default match settings were applied, and the same master gel was selected for both aligned and unaligned images. This was the same gel used as the top reference gel in Progenesis. The "Give Manual Guidance" and "Test Settings" features of the Advanced Spot Detection Wizard were used. The speckle filter and the vertical and horizontal streak filter in the Advanced Controls were also used, as recommended by the manufacturer. Using these settings a similar number of spots was obtained to that reported by Nishihara and Champion using an earlier version of this program. Again, spot volumes were not normalized. No manual editing of the data was performed. The data were simply exported to Excel and spots present in 3 of 4 replicates in the Nishihara and Champion series, or 3 of 3 replicates in the SH-SY5Y dilution series determined.

For PDQuest and Progenesis, three different strategies were considered for dealing with the missing spot problem. The first was to simply substitute zeros for missing spot values. This strategy leads to biased quantifications, since undetected spots are frequently not truly absent, but present below some unknown detection limit on the gel. The second strategy was to restrict the analysis to spots present on all gels. This eliminated the missing data problem, but as shown in the results, greatly reduced the number of spots considered in the analysis. Spots excluded using this strategy could be of great significance, representing proteins that are abundant in one group but nearly absent in another. The third strategy was to average over only the replicates in which the spot was detected. For example, given triplicate gels, if a specific protein spot was present in ⅔ gels, then the average of the two quantifications was taken. If a spot was present in 0/3 or ⅓ gels, then zero was used for the quantification. This strategy also led to biased quantifications. The first strategy was used substituting zeros for missing values for the analyses, since it performed the best of the three alternatives (data not shown).

A Method of the Present Invention

The method assumes that gel images have been scanned without pixel saturation and suitably aligned. These images were aligned using the commercially-available TT900 program (Nonlinear Dynamics), although any effective image alignment program could have been used. For optimal performance of this method, any remaining misalignment should be less than the minimum distance between the pinnacles of two adjacent protein spots.

Once the gel images were aligned, the following steps were performed in an exemplary implementation of method of the invention:

1. Baseline correct individual gel images. For baseline correction, the global minimum pixel intensity on each gel image from every pixel on the gel image was subtracted. The gel images were not normalized in these dilution series experiments, since normalization would factor out the protein load differences that one wants to exploit to assess quantification reliability. Under normal circumstances, one would normalize by dividing by the average pixel intensity on the gel image. This would adjust for different amounts of total protein loaded on each gel, and cause the average normalized intensity on each gel image to be 1.0.

2. Generate the average gel image. The average gel image was generated by averaging the baseline-corrected intensity pixel-by-pixel across all gel images in the experiment. This "average gel image" differs from the composite gel images constructed by PDQuest, Progenesis, and other commercial software that are representations of the spots detected on all of the gel images rather than simple pixel-wise averages.

3. De-noise the average gel image using wavelet shrinkage. Wavelet-based de-noising filters were applied to de-noise the average gel. On these gel images, wavelet de-noising "smoothes out" small irregularities in the average gel image that are consistent with white noise while retaining the larger signals produced by true protein spots. Removal of these irregularities reduces the number of false positive spots detected. Wavelet de-noising was accomplished using the 2-dimensional undecimated discrete wavelet transform (2-D UDWT), as implemented in version 2.4 of the Rice Wavelet Toolbox (RWT), which is freely available from their web site (http://www-dsp.rice.edu/software/rwt.shtml). De-noising was accomplished using three steps. First, given a particular choice of wavelet basis, wavelet coefficients were computed for the average gel image. These coefficients represented a frequency-location decomposition in both dimensions of the image. The advantage of using the UDWT over the more computationally efficient and commonly used dyadic wavelet transform (DDWT) is that the results are translation-invariant, meaning that the de-noising is the same even if you shift or crop the image in either dimension. The results are minimally sensitive to choice of wavelet basis; the Daubechies wavelet with 4 vanishing moments was used for these analyses. Second, hard thresholding was applied to the wavelet coefficients. By hard thresholding, all coefficients whose magnitude was below a threshold $\phi=\delta\sigma$ were set to a value of "0", while leaving all coefficients with magnitudes $\geq \phi$ unaffected. The parameter $\sigma$ represents a robust estimator of the standard deviation, following Donoho and Johnstone by using the median absolute deviation for the highest frequency wavelet coefficients divided by 0.6745, and $\delta$ is a threshold parameter specified by the user, with larger choices of this parameter result in more de-noising. In the context of the MALDI-MS technique, values of $\delta$ between 5 and 20 were suggested. For 2D gels, the background white noise is not as strong as that found in the MALDI-MS technique, so smaller values work better. In the instant case, $\delta=2$ was used, which is the default value in this implementation of the method of the present invention. Third, the de-noised average gel image was generated by applying the inverse transform of the UDWT to the thresholded wavelet coefficients. The thresholding works because white noise is equally distributed among all wavelet coefficients, while the signal is focused on a small number of coefficients. Thus, the thresholding zeroes out the large number of wavelet coefficients of small magnitude corresponding mostly to noise, while leaving the small number of coefficients of large magnitude corresponding to signal.

4. Detect pinnacles on wavelet de-noised average gel image. All pinnacles on the wavelet de-noised average gel were detected. A pixel location contained a pinnacle if it's intensity was a local maximum in both the horizontal and vertical directions on the gel image, and if its intensity was greater than the $75^{th}$ percentile on the gel image. This threshold can be changed if desired. After this step, a list of pixel coordinates marking the pinnacles in the average gel image was obtained.

5. Combine spots with pinnacles within ±2 Pixels. If any pinnacles were found within a 5×5 square pixel array surrounding another pinnacle, then these pinnacles were combined by keeping only the one with the highest intensity. It is rare to see two protein spots with pinnacles less than 5 pixels from each other, given the resolution of the scanner, which yields a 1024×1024 pixel image of the gel. Thus, it does not appear that spots are lost by this step, which has the benefits of removing spurious double-peaks and accommodating imperfect alignment in the quantification, as described in the next step. If desired, any neighborhood size can be substituted for the value of 5.

6. Quantify each spot by the maximum pinnacle intensity. For each gel image, each spot was quantified by the maximum intensity within the 5×5 square pixel array formed by taking the corresponding pinnacle location in the average gel image and extending out +/−2 pixels in the horizontal and vertical directions. This tolerance enabled the maximum pinnacle intensity to be found for the corresponding spot for each individual gel image even when the alignment was not perfect. The accuracy of the alignment only needed to be within ±2 pixels in both the horizontal and vertical directions. Given N gel images and p spots, after this step an N×p matrix of protein expression levels Y with no missing values was left. It is recommended that the log-transform of these expression levels be used for subsequent analysis. In profiling studies, this matrix would be analyzed to find which of the p spots appear to be associated with factors of interest, and worthy of future study.

Experimental Methods: Statistical Analysis

For each study, the total number of detected spots was listed. For Progenesis and PDQuest results, the number of these that were "unmatched" was computed, meaning that they were present on only one gel image and not matched to any spot on any other gel image. The above implementation of the method of the present invention had no unmatched spots since by definition it yielded quantifications for every pinnacle on each gel image. All unmatched spots were removed in Progenesis and PDQuest from consideration in the quantitative summaries. Any spots that were not present in at least 3 out of 4 replicate gel images for at least one of the protein load groups in the Nishihara and Champion study or 3 out of 3 replicates in the SH-SY5Y cell dilution series were also removed. This criterion was applied by Nishihara and Champion in their previous study, and is a criterion commonly used by many investigators.

The results of the dilution series experiments were used to assess the matching percentage, reliability, and precision of the different methods' quantifications. The matching percentage for the above implementation of the present method applied to aligned gels was 100%. For PDQuest and Progenesis, the matching percentage was estimated by randomly selecting 10% of the total number of spots that met the above criteria, and then checking by hand the number of times the automatic algorithms correctly matched the corresponding spot on all individual gels for which it was detected to the spot on the reference gel. Note that this measure only deals with matching errors, not detection errors, since gels for which a given spot was not detected at all did not count as a mismatch in terms of the match percentage. Also, incorrect spot splitting (e.g., matching a spot in one gel to the same spot and an adjacent one which were detected as one spot in another gel) was not considered a mismatch in this analysis.

Reliability of quantification for each spot was assessed by computing the coefficient of determination ($R^2$) from a simple linear regression (implemented in Matlab, Mathworks, Inc.) of the mean spot quantification across replicates for each protein load group versus the true protein load. If the correlation (R) was negative, then $R^2=0$ was set. This measure was computed for all detected spots, not just a select set, so a realistic assessment of the performance of each method across the entire gel could be obtained. The $R^2$ across all spots within a gel was summarized by the mean, five-number summary ($5^{th}$ percentile, Q05, $25^{th}$ percentile, Q25, the median, Q50, the $75^{th}$ percentile, Q75, and the $95^{th}$ percentile, Q95), and by counting the number of "reliable spots." Spots were considered reliable if $R^2>0.90$, which roughly corresponds to a correlation of at least 0.95 between the group mean spot quantifications and the protein load. The number of "reliable spots" provided a sense of the number of spots that were well quantified by the different methods.

The precision of the quantifications was assessed by computing the coefficient of variation (% CV) for each spot detected in the entire gel set across the gels within each protein load group. In the description above, the results from the 30 µg protein load group for the Nishihara and Champion dilution series are presented (as they did in their paper), and in the 50 µg group for the SH-SY5Y dilution series; other results are available in accompanying tables. The % CV across all spots was summarized by the mean and 5 number summary (Q05, Q25, Q50, Q75, Q95), and the number of detected spots with % CV<20 was counted. Note that it was not possible to compute CVs for spots with group mean quantifications of zero, so those spots were left out of this analysis.

TABLE 1

Reliability of Quantifications for Detected Spots - provides a summary of $R^2$ measuring linearity of quantification method across protein loads within dilution series for all spots automatically detected by the method of the invention (Pinn) and for spots meeting the selection criteria below for PDQuest (PDQ) and Progenesis (Prog). Software settings are detailed in the Methods. No manual editing of the datasets was performed. PDQuest and Progenesis were run on the gel sets without alignment, since that is typically how these programs are used. Programs were also run on the aligned gels (PDQ-a and Prog-a) to verify that the superior performance of the present method was not solely due to image alignment. The summaries include match percentage, number of spots, number of reliable spots, and the mean, median, $5^{th}$ percentile, $25^{th}$ percentile, $75^{th}$ percentile, and $95^{th}$ percentile for the distribution of $R^2$ across spots. A spot was considered reliable if $R^2 > 0.90$.

| Study | Method | Match Percent | Number of Spots* | Reliable Spots ($R^2 > 0.90$) | $R^2$ Mean | Q05 | Q25 | Median | Q75 | Q95 |
|---|---|---|---|---|---|---|---|---|---|---|
| N + C | Pinn | 100% | 1380 | 1146 | 0.931 | 0.754 | 0.931 | 0.972 | 0.989 | 0.996 |
|  | PDQ | 60% | 1376 | 847 | 0.835 | 0.206 | 0.790 | 0.941 | 0.984 | 0.995 |
|  | Prog | 84% | 875 | 666 | 0.883 | 0.253 | 0.909 | 0.973 | 0.990 | 0.996 |
|  | PDQ-a | 71% | 1342 | 869 | 0.850 | 0.322 | 0.829 | 0.944 | 0.982 | 0.994 |
|  | Prog-a | 80% | 887 | 713 | 0.894 | 0.446 | 0.919 | 0.963 | 0.981 | 0.990 |
| SH-SY5Y | Pinn | 100% | 1013 | 663 | 0.905 | 0.764 | 0.874 | 0.929 | 0.961 | 0.987 |
|  | PDQ | 45% | 1297 | 406 | 0.735 | 0.141 | 0.637 | 0.820 | 0.923 | 0.982 |
|  | Prog | 30% | 979 | 295 | 0.662 | 0.011 | 0.448 | 0.805 | 0.919 | 0.981 |
|  | PDQ-a | 64% | 1103 | 391 | 0.753 | 0.137 | 0.669 | 0.841 | 0.931 | 0.980 |
|  | Prog-a | 43% | 1092 | 384 | 0.698 | 0.014 | 0.570 | 0.845 | 0.932 | 0.982 |

*For Progenesis and PDQuest, the number of spots corresponds to the number of spots used in the quantitative analysis, which are those present in at least 3/4 replicate gels within at least 1 of the 7 protein load groups for the Nishihara and Champion study, and at least 3/3 replicate gels within at least 1 of the 6 protein load groups for the SH-SY5Y study.

TABLE 2

Precision of Quantifications for Detected Spots - provides a summary of coefficient of variation (% CV) for the 30 μg protein load for the Nishihara and Champion study, and the 50 μg load for the SH-SY5Y cell study, for all spots automatically detected by the method of the invention (Pinn) and for spots meeting the selection criteria below for PDQuest (PDQ) and Progenesis (Prog). Software settings are detailed in the Methods. No manual editing of the datasets was performed. PDQuest and Progenesis were run on the gel sets before alignment, since that is typically how these programs are used. These programs were also run on the aligned gels (PDQ-a and Prog-a) to verify that the superior performance of the present method was not solely due to image alignment. The summaries include the number of spots, plus the mean, median, $5^{th}$ percentile, $25^{th}$ percentile, $75^{th}$ percentile, and $95^{th}$ percentile for the distribution of % CV across spots, and the number of spots with % CV < 20. The % CV results for the other protein load groups are presented in supplementary tables.

| Study | Method | Number of Spots* | Number of spots with % CV < 20 | % CV Mean | Q05 | Q25 | Median | Q75 | Q95 |
|---|---|---|---|---|---|---|---|---|---|
| N + C | Pinn | 1380 | 902 | 18.1 | 6.8 | 13.2 | 17.7 | 22.0 | 29.6 |
|  | PDQ | 1326 | 498 | 54.7 | 6.5 | 14.4 | 27.5 | 77.5 | 200.0 |
|  | Prog | 821 | 304 | 40.3 | 11.1 | 16.9 | 23.6 | 41.3 | 121.8 |
|  | PDQ-a | 1309 | 415 | 55.7 | 9.5 | 17.7 | 29.8 | 76.1 | 200.0 |
|  | Prog-a | 852 | 144 | 47.4 | 14.4 | 22.6 | 30.5 | 50.3 | 145.5 |
| SH-SY5Y | Pinn | 1013 | 859 | 12.2 | 2.0 | 5.1 | 9.5 | 16.1 | 30.8 |
|  | PDQ | 1166 | 267 | 64.4 | 8.0 | 21.4 | 45.5 | 91.1 | 173.2 |
|  | Prog | 787 | 188 | 53.2 | 8.1 | 20.6 | 36.9 | 86.6 | 173.2 |
|  | PDQ-a | 1001 | 272 | 58.8 | 7.0 | 19.0 | 38.0 | 88.1 | 173.2 |
|  | Prog-a | 931 | 182 | 59.9 | 8.2 | 24.2 | 45.5 | 88.9 | 173.2 |

*The number of spots in this table corresponds to the number of spots from Table 1 for which there was at least one non-missing value for the 30 μg group in the Nishihara and Champion Study, and the 50 μg group in the SH-SY5Y study, since it is not possible to compute CVs for spots with group means of zero.

The Myth of Automated, High-Throughput 2-Dimensional Gel Analysis

Many software packages have been developed to process and analyze 2D gel images. Some programs have been touted as automated, high-throughput solutions. In this study, five commercially available programs were tested using 18 replicate gels of a rat brain protein extract. The following variables were determined: computer processing time; approximate spot editing time; time required to correct spot mismatches; total processing time; the number of spots automatically detected; the number of spots kept after manual editing; and the percentage of automatically generated correct matches. The effect of increasing the number of replicate gels on spot matching efficiency for two of the programs was also determined. For all programs tested, it was found that less than 3% of the total processing time was automated. The remainder of the time was spent in manual, subjective editing of detected spots and computer generated matches. Total processing time for 18 gels varied from 22-84 hours. The percentage of correct matches generated automatically varied from 1% to 62%. icreasing the number of gels in an experiment dramatically reduced the percentage of automatically generated correct matches. These results demonstrate that such 2D gel analysis programs are not automatic or rapid, and also suggest that matching accuracy decreases as experiment size increases.

1. Introduction 2-dimensional gel electrophoresis (2DE) is the oldest technology widely used in proteomics, having first been described in 1975. 2DE gained a reputation for poor reproducibility and technical difficulty. Recent years have seen remarkable improvements in the reliability and ease of use of proteomic technologies. Developments that have helped improve 2DE included the development of immobilized pH gradient (IPG) strips, use of sample prefractionation to decrease sample complexity and increase the detection of lower abundance proteins, as well as new reagents that help improve the recovery of membrane and highly basic proteins. However, accurate, unbiased, and rapid gel analysis has persisted as a major bottleneck. In 2001, Fey and Larsen stated that "There is no program that is remotely automatic when presented with complex 2DE images" . . . "most programs require often more than a day of user hands-on time to edit the image before it can be fully entered into the database."

The general algorithm followed by these packages is to first detect spots on all gels, then match cognate spots across gels. Numerous software packages have come and gone, all purporting to provide accurate gel analysis and more recently, automation and improved throughput. There have been several tests of these packages in recent years. In most cases, all packages are reported to function reasonably well. However, the types of samples evaluated, as well as the number of gels considered, are not reflective of current, ever-expanding proteomics experiments. Tests have been performed either using artificial gels, actual gels with relatively few replicates, replicates generated by artificial image distortion, or investigating only selected spots within a gel. In these studies, only one or at most two software programs were evaluated at any one time, making generalized comparisons difficult. Also, individual studies did not comprehensively evaluate spot detection, matching percentages, as well as time required for both the automatic, computer generated analyses and subsequent manual editing time needed.

In this study, a set of 18 replicate gels were used to assess all of the above parameters in five different software programs. We also expanded the set to include 27 gels to better determine the effect of increasing experiment size on automatic match efficiency. There was a wide variation in the number of spots automatically detected by the programs, as well as in the percentage of correct matches generated automatically. All software packages required extensive and time consuming manual editing and correction. It was also determined that the percentage of correctly matched spots decreased markedly as the number of gels included in an experiment increased.

2. Materials and Methods

2.1 Gels Used for Analysis

Gels were loaded with 10 mcg of a wide range rat brain protein extract from the nucleus accumbens region of 27 individual rats (1 gel per rat) performed using the ProteoPrep™ (Sigma) kit. Brain tissue was suspension was ultrasonicated in extraction buffer on ice for 15-second bursts at 70% amplitude for a total time of 1 minute, and then centrifuged at 14,000×g for 45 minutes at 15° C. to pellet any insoluble material. The proteins in this supernatant were then reduced for 1 hour at room temperature by adding tributylphosphine to a final concentration of 5 mM and alkylated in the dark for 1.5 hours at room temperature by adding iodoacetamide to a final concentration of 15 mM. Protein concentration was determined using the Bradford assay. Samples were then used for rehydration of immobilized pH gradient (IPG) strips. 11 cm pH 3-10 IPG strips (Proteome Systems, Sydney, NSW Australia) were rehydrated with 90 μl of rehydration buffer. 90 μl of the protein sample solution was then added to the strip, and then focused on the Proteome Systems IEF Cell for 6 h using a 100-3,000 V slow ramp gradient. Then, a linear ramp from 3-10,000 V over 3 hours was followed by 10 additional hours at 10,000 V. Focused strips were then equilibrated in SDS-equilibration buffer and loaded onto 6-15% polyacrylamide gradient gels (GelChips, Proteome Systems) using GelChips Tris/tricine buffer for separation in the second dimension. Run conditions were 50 mA/gel until the bromophenol blue reached the end of the gel. Gels were then stained overnight using Sypro Ruby. Gel images were then obtained using an Alpha Innotech MultiImage (Alpha Innotech, San Leandro, Calif.) light cabinet.

2.2 Software Packages

Software packages were considered for evaluation if they were commercially available at the time of the study. Previously developed packages that were no longer being sold were not included. Also, programs that were repackaged "clones" of other programs were excluded. The five programs that were evaluated completely are shown in Table 3. All programs were run on a Dell Workstation 470 with dual Xeon 3.2 gHz processors and 4 GB RAM running Windows XP.

TABLE 3

Software Packages Evaluated

| Software | Version | Company | Website |
|---|---|---|---|
| Delta 2D | 3.3 | Decodon | http://www.decodon.com/ |
| ImageMaster Platinum | 6 | GE Healthcare | http://www.gehealthcare.com/usen/index.html |
| PDQuest | 8 | Biorad | http://www.biorad.com/ |
| Progenesis Discovery | 2005 | Nonlinear Dynamics | http://www.nonlinear.com/ |
| ProteinMine | 2005 | BioImagene | http://www.bioimagene.com/proteinmine.html |

2.3 Outcome Variables

Two goals of this study were to determine how automated the gel analysis process was and how long the process took when "real world" gels were used for analysis. Prior to beginning analyses, software familiarization was accomplished by reading any available documentation as well as performing any supplied tutorials. Technical support was contacted as needed. This time was not included in the total analysis time. It was determined that the average number of spots per gel initially detected automatically by each program and the average number of spots after manual editing to remove artifacts, correct inaccurate splits of group spots, and add missed spots. The amount of time needed to perform this editing was also determined. Subsequently, the percentage of post-edited ("real") spots that were correctly matched by the initial automated matching algorithm was determined. This was accomplished by randomly sampling 15% of the total number of post-edited spots and using those spots for analysis. It was then determined whether it was possible to obtain 100% correct matching with each program as well as the time needed to manually correct mismatches. The above steps were summed to produce a total processing time for each gel set. Spot counts and matches were verified by the senior author; however this time was not included in the totals. Subjective comparisons of ease of use, time needed to master the program, and ability of the software to visualize the data (spots) were also reported.

2.4 Analysis Parameters

Gel spot detection was performed starting with default or typical settings recommended by each manufacturer. Subsequently, these settings were optimized on a randomly selected subset of the gels to detect the maximum number of "real" spots while minimizing the detection of artifacts. The settings used were: for Delta 2D, background region=32, sensitivity percentage=10, average spot size=20, create modeled spots was selected, and union fusion gel was also selected. In Image Master, the alignment option selected was global. Spot parameter optimization settings were: smoothing=1, minimum area=15, saliency=100. Additional settings were intensity=500, area=3.5. For PDQuest, the spot detection parameter wizard was used. Settings were sensitivity=35.4, size scale=3, minimum peak—358. Optional controls streak correction settings were vertical=29 and horizontal=75. In Progenesis, the analysis wizard was used. Progenesis background subtraction method was selected, and the combined warp-match setting was also chosen. Normalization was to total spot volume. Minimum spot area=2, split factor=9. For ProteinMine, gel processing settings were: sensitivity=80, spot outline=65, minimum size=10. Detailed spot detection was also selected. Filter parameters were: average intensity 600, quality=3613, core penumbra=0.04. Alignment settings were neighborhood size=25, distortion magnitude=75, match threshold=25, alignment fidelity=25. One way ANOVA with Tukey post-hoc test was performed using InStat (Graph Pad software). $P<0.05$ was required for significance.

All packages required the selection of a reference gel. This was done automatically by PDQuest (gel a2) and Progenesis (gel a17). The other three programs required manual selection of the reference gel. We chose gel a17 as the reference gel for Delta 2D, Protein Mine and Image Master.

3. Results

3.1 Spot Detection

Using manufacturer recommended settings, the programs automatically detected widely divergent numbers of spots, ranging from a low of 568±134 for ImageMaster to 1471+/−268 for Progenesis (Table 4).

TABLE 4

Spot Detection Results

| Program | Avg. spot # detected automatically | Avg. spot # after manual editing | Approximate spot editing time (18 gels) |
|---|---|---|---|
| Delta 2D | 820 ± 0 | $^{\$\&}$846 ± 0 | $^{\&}$1 hr |
| ImageMaster | 568 ± 134 | $^{\$}$626 ± 68 | 22 hrs |
| PDQuest | *1395 ± 639 | 703 ± 35 | 10 hrs |

TABLE 4-continued

Spot Detection Results

| Program | Avg. spot # detected automatically | Avg. spot # after manual editing | Approximate spot editing time (18 gels) |
|---|---|---|---|
| Progenesis | *1471 ± 268 | 674 ± 32 | 18 hrs |
| ProteinMine | 893 ± 380 | 706 ± 60 | 18 hrs |

*Significantly more spots detected automatically by PDQuest and Progenesis than other programs ($P < 0.001$). Totals for ImageMaster, ProteinMine, and Delta 2D were not significantly different from each other.
$Significantly different edited spot counts than PDQuest, Progenesis, and ProteinMine ($P < 0.05$).
&Delta 2D used a different workflow than the other packages. Gels were warped, and then spot editing performed on an artificial "fusion" gel. The time to edit spots on the fusion gel was similar to the time required to edit a normal gel.

PDQuest and Progenesis automatically detected significantly more spots than the other three programs. The lack of variability obtained for Delta 2D is not directly comparable to the other programs, as a different preprocessing algorithm is used. Rather than detecting spots on each individual gel and then warping gels or drawing vectors to match cognate spots, in Delta 2D spots are first warped to each other, then spot detection is performed on an artificially created "fusion gel" generated from the dataset. This "spot mask" is then applied to all the replicate gels. The spot count after manual editing also varied between programs, but not as widely as after automatic detection. The total spot counts of ProteinMine, PDQuest, and Progenesis after manual editing were not significantly different from each other. However, ImageMaster had significantly fewer spots then all the other packages, while Delta 2D had significantly more ($P<0.05$; Tukey post-hoc test). In contrast with the other packages, ImageMaster detected far fewer spots and required a net addition, rather than removal, of spots when manufacturer's recommended settings were used. The amount of time required for manual spot editing was substantial, ranging from ¾-1¼ hrs per gel (Delta 2D excluded). FIG. 1 shows the same replicate gel (except for Delta 2D, where the fusion gel is shown) after spot detection and manual editing using each individual software program.

3.2 Spot Matching

After spot detection, all of the packages except Delta 2D matched spots across all gels. In Delta 2D, spots that were detected in the fusion gel were applied as a "mask" to all gels that were previously warped. Thus, by definition matching for Delta 2D was 100%, although the warping and matching process was entirely manual. Automatic matching percentages were fairly poor for all the other programs, ranging from 1% correct for ImageMaster to 62% for ProteinMine. Manually setting only two landmarks dramatically improved the performance of ImageMaster, increasing automatic match percentage to 76%. Setting landmarks did not have such a dramatic effect on either Progenesis (21 landmarks) or PDQuest (2 landmarks), and was not possible in ProteinMine (Table 5).

TABLE 5

Spot Matching Results

| Program | % automatically matched correctly | % automatically matched correctly after landmarks | Maximum % correct matches obtainable | Approximate spot matching time (18 gels) |
|---|---|---|---|---|
| Delta 2D | *0% | 100% | 100% | 18 hrs |
| ImageMaster | 1% | 76% | 76% | 14 hrs |
| PDQuest | 50% | 51% | 100% | 18 hrs |
| Progenesis | 49% | 57% | 61% | 65 hrs |
| ProteinMine | 62% | #n/a | 100% | 18 hrs |

*Matching is completely manual in Delta 2D, and 100% by definition
Cannot set landmarks in ProteinMine Surprisingly, we could not achieve 100% matching with two of the programs (Progenesis and ImageMaster) in spite of extensive hand editing and consultation with the companies. Most of the programs required a similar, yet substantial amount of time and manual effort for accurate spot matching ("warping" in the case of Delta 2D; Table 3). Manual editing times for Progenesis averaged 3-4 times longer than the other packages. The reasons for this appeared to be the algorithmic design, which required reprocessing after each round of match corrections, and a flaw in the algorithm that would make new matches incorrect once others had been corrected.

3.3 Total Analysis Time and Ease of Use

The total amount of time taken to analyze 18 gels using each of the software packages is presented in Table 6. Delta 2D had the shortest overall analysis time of approximately 22 hours. Analysis using Progenesis took nearly four times as long, at 84 hours. PDQuest, ProteinMine, and ImageMaster had total analysis times between 30-36 hours. It should be noted that in all cases, the automated portion of the analysis was only a tiny fraction of the time required. No more than 3% of the total analysis time was automated by the computer. The bulk of the time was spent in manual, subjective editing of spots and spot matches.

TABLE 6

Approximate Total Gel Processing Times

| Program | Computer Processing | Spot Editing | Spot Matching | Total Time |
|---|---|---|---|---|
| Delta 2D | 15 min | 1 hr | 21 hrs | 22 hrs |
| ImageMaster | 1 hr | 22 hrs | 10 hrs | 33 hrs |
| PDQuest | 3 min | 18 hrs | 12 hrs | 30 hrs |
| Progenesis | 1 hr | 18 hrs | 65 hrs | 84 hrs |
| ProteinMine | 20 min | 18 hrs | 18 hrs | 36 hrs |

The "user-friendliness" of the programs was evaluated by comparing relative ease of use, the amount of time needed to master use of each software package, and the ability to visualize and compare the gel spots in various ways, which can be a tremendous aid in differentiating spots from artifacts (Table 7).

TABLE 7

User Friendliness

| Program | Ease of Use | Time Needed to Master Program | Data Visualization |
|---|---|---|---|
| Delta 2D | Very easy | Less than 1 week | Good |
| ImageMaster | Relatively difficult | 1-2 weeks | Fair |
| PDQuest | Easy; straightforward user interface | 1 week | Excellent |

TABLE 7-continued

User Friendliness

| Program | Ease of Use | Time Needed to Master Program | Data Visualization |
|---|---|---|---|
| Progenesis | Very difficult; pretty interface, but very complex | 1 month, and multiple sessions with field technician | Excellent |
| ProteinMine | Interface somewhat cumbersome, but straightforward | 1 week | Good |

Relative ease of use included a subjective evaluation of the intuitiveness of the user interface and the ease of performing routine analytical procedures. As seen in Table 7, ease of use varied considerably between the packages. As would be expected, the time needed to master each program depended on how easy the program was to navigate. There did not appear to be a direct correlation between ease of use and total analysis time (Table 6).

3.4 Does the Number of Gels Affect Spot Matching Efficiency?

An experiment was performed to determine the effect of increasing the number of replicate gels in an experiment would be on automatic matching. For this experiment, groups of 3, 9, 18, and all 27 of the replicate gels were analyzed using both PDQuest and Progenesis. After spot detection and manual spot editing as described above, automatic matching was performed without placing any manual landmarks. The percentage of spots correctly matched was evaluated for each group as described above. This data is presented in Table 7. These results clearly demonstrate that the accuracy of matching decreases as the number of gels analyzed increases. PDQuest and Progenesis appeared to have similar accuracies for matching 3, 9, and 18 replicate gels. However, the accuracy of Progenesis appears to decrease much more rapidly than that of PDQuest when the number of gels included was increased from 18 to 27 (Table 8).

TABLE 8

Percent Correct Automatic Spot Matches Decrease as Experiment Size Increases

| # of Gels in Experiment | PDQuest | Progenesis |
|---|---|---|
| 3 | 88% | 96% |
| 9 | 70% | 66% |
| 18 | 50% | 49% |
| 27 | 42% | 21% |

4. Discussion

In this study, the effectiveness of commercially available software programs in analyzing a moderate sized gel series were evaluated. The automated portion of the analysis was less than 3% of the total time needed for optimization, which ranged from about 1-4 hours per gel. While this is still far less than the 1 day per gel estimated by Fey and Larsen, it remains onerous. It was also determined that increasing experiment size degraded the performance of two of the programs, suggesting that as experiments increase in size, the amount of analysis time needed per gel would also increase. Thus, in spite of any claims to the contrary, 2D gel analysis remains a very manual, subjective, and labor intensive process.

While 4 out of the 5 packages used a similar workflow, the individual algorithms showed a wide range of variation in both spot detection and matching ability. The average number of spots detected by the packages ranged from 568 for ImageMaster to 1471 for Progenesis. As the algorithms used for spot detection are proprietary, the reasons for this wide variation are not clear. Surprisingly, there is still some variation in overall spot number after manual editing. This variation is not as dramatic as that in automatically generated spots (626 to 846 spots), but is still concerning. Some gel to gel variation would be expected. However, the variation is at least partly dependent on the program's ability to adjust gel contrast and brightness, as well as the presence of other visualization tools (e.g., 3D contour reconstruction). It is often difficult to positively identify faint protein spots, thus differences in program settings could bias visual confirmation. Taken together, these observations suggest that what looks like a spot to the human eye may not be the best "gold standard" for gel analysis, as previously suggested.

An extremely wide degree of variation in automated matching performance was also seen, ranging from 0% for Delta 2D, which could not match spots automatically, to 62% for ProteinMine. A great deal of painstaking, subjective work was required to correct mismatches. It was not possible for us to achieve 100% matching with either ImageMaster or Progenesis. The reasons for this are unclear due to the proprietary nature of the spot matching algorithms. However, it is something to keep in mind when using these programs to analyze larger gel sets. The unique algorithm employed by Delta 2D enabled 100% matching, but was entirely manual. Also, difficulties with data export for statistical analysis greatly hindered the use of this program. It was further demonstrated that the performance of both PDQuest and Progenesis is excellent with small gel series, but degrades rapidly as the number of gels increases. As proteomics experiments are becoming more and more ambitious, this finding is very concerning. An increase in subjective manual editing may increase variability due to the visual factors mentioned above. Also, the issue of bias, although rarely intentional, is much more likely to creep into an experiment when subjective editing comprises the bulk of the workflow.

How the problems of both increasing automated performance and decreasing subjectivity be resolved as experiment size increases? A clue to a possible solution may be found in the workflow adopted by Delta 2D. The standard work flow consists of identifying spots and defining spot boundaries on individual gels, then matching corresponding spots across gels. These are quite computationally intensive tasks, requiring complex and error-prone algorithms. As demonstrated, performance of these algorithms worsens when more gels are added to the analysis. Delta 2D first aligns cognate features across gels, then does spot detection and boundary determination on an artificially created "fusion gel" that is a representation of spots present on all gels. This "spot mask" is then applied to all gels. This approach can save some time, as shown in Table 6. However, the process as implemented in Delta 2D is completely manual, and thus susceptible to subjective bias. An automated approach to aligning cognate gel features has been developed by Dowsey and colleagues. This promising development warrants further investigation and application.

However, none of these methods adequately address the issue of spot detection, which is the determination of what are and are not "real" spots, or the question of where a spot begins and ends. Both of these are difficult issues that are prone to introduce measurement variability. The invention proposes a method that utilizes feature alignment as the first stage of the workflow, then sums all gels to create an "average gel." In this way, "real" spots are reinforced across gels, while artifacts are averaged out. By the central limit theorem, any spot that is present in greater than sqrt (n) gels should be visible on the average gel. In addition, instead of using complex algorithms to define spot boundaries, peak values in the horizontal and vertical dimensions ("pinnacles") are used to define spots. This algorithm is fast and entirely automatic, capable of processing 60 gels in under a minute. Novel methods to automate spot matching and detection such as the two described above hold the promise of dramatically improving both the throughput and objectivity of 2D gel analysis.

In conclusion, currently available commercial software packages designed for 2D gel analysis are time consuming and only minimally automated. However, several recent developments as well as improvements to existing software packages may help improve the speed and accuracy of analysis so that the rapid, objective analysis of large 2D gel experiments evolves from myth to reality.

Method for Detecting and Quantifying Protein Spots in 2-Dimensional Gel Electrophoresis Data One of the key limitations for proteomic studies using 2-dimensional gel electrophoresis (2DE) is the lack of rapid, robust, and reproducible methods for detecting, matching, and quantifying protein spots. The most commonly used approaches involve first detecting spots and drawing spot boundaries on individual gels, then matching spots across gels, and finally quantifying each spot by calculating normalized spot volumes. This approach is time consuming, error-prone, and frequently requires extensive manual editing, which can unintentionally introduce bias into the results.

Results:

The invention provides a new method for spot detection and quantification called "Pinnacle" that is automatic, quick, sensitive and specific, and yields spot quantifications that are reliable and precise. This method incorporates a spot definition that is based on simple, straightforward criteria rather than complex arbitrary definitions, and results in no missing data. Using dilution series for validation, we demonstrate Pinnacle outperformed two well-established 2DE analysis packages, proving to be more accurate and yielding smaller CVs. More accurate quantifications may lead to increased power for detecting differentially expressed spots, an idea supported by the results of the group comparison experiment. The fast, automatic analysis method makes it feasible to conduct very large 2DE-based proteomic studies that are adequately powered to find important protein expression differences.

1.0 Introduction

Proteomics is capable of generating new hypotheses about the mechanisms underlying physiological changes. The perceived advantage of proteomics over gene-based global profiling approaches is that proteins are the most common effector molecules in cells. Changes in gene expression may not be reflected by changes in protein expression (see, e.g., Anderson and Seilhammer 1997, Gygi, et al. 1999). However, the large number of amino acids and post-translational modifications make the complexity inherent in analyzing proteomics data greater than for genomics data.

Several methods have been developed for separating proteins extracted from cells for identification and analysis of differential expression. One of the oldest yet still most widely used is 2-dimensional gel electrophoresis (2DE, Klose 1975, O'Farrell 1975). In this method, proteins are first separated in one direction by their isoelectric points, and then in a perpendicular direction by molecular weight. As 2DE-based proteomic studies have become larger and more complex, one of the major challenges has been to develop efficient and effective methods for detecting, matching, and quantifying spots on large numbers of gel images. These steps extract the rich information contained in the gels, so are crucial to perform accurately if one is to make valid discoveries.

In current practice, the most commonly used spot detection and quantification approach involves three steps. First, a spot detection method is applied to each individual gel to find all protein spots and draw their boundaries. Second, spots detected on individual gels are matched to a master list of spots on a chosen reference gel, requiring specification of vertical and horizontal tolerances since spots on different gels are rarely perfectly aligned with one another. Third, "volumes" are computed for each spot on each gel by summing all pixel values within the defined spot regions.

Unfortunately, methods based on this approach lack robustness. Errors are frequent and especially problematic for studies involving large numbers of gels. The errors consist of three main types, spot detection, spot boundary estimation, and spot matching errors. Detection errors include merging two spots into one, splitting a single spot into two, not detecting a spot, and mistaking artifacts for spots. Also, automatically detected spot boundaries can be inaccurate, increasing the variability of spot volume calculations. Matching errors occur when spots on different gels are matched together but do not correspond to the same protein. In our experience, these errors are pervasive and can obscure the identification of differential protein expression. Almeida, et al. (2005) list mismatched spots as one of the major sources of variability in 2DE, and Cutler, et al. (2003) identify the subjective nature of the editing required to correct these errors as a major problem. Extensive hand editing is needed to correct these various errors and can be very time-consuming, taking 1 to 4 hours per gel (Cutler, et al. 2003). Taken together, these factors limit throughput and bring the objectivity and reproducibility of results into question. Also, one must decide what to do about missing values caused by spots that are matched across some, but not all gels. A number of ad hoc strategies have been employed, but all have their weaknesses and result in biased quantifications.

According to the invention, a new method is provided for spot detection and quantification for 2DE analysis. This method takes a different fundamental approach than the most commonly used methods, using a mean gel for spot detection and using pinnacles instead of volumes for spot quantification. As a result of these differences, this method is much simpler and quicker than existing alternatives, and it results in no missing data, more sensitive and specific spot detection, and as we demonstrate in validation studies, spot quantifications that are more accurate and precise. Section 2 describes and motivates the Pinnacle algorithm. Section 3 describes the validation and group comparison studies, providing details of the data sets used, the implementation details for the competing methods, and the statistical measures used or evaluation. Section 4 contains the results of the validation and group comparison studies, and Sections 5 and 6 contain a discussion of the benefits of using Pinnacle for spot detection and quantification, and final conclusions.

2.0 Methods

The method assumes that gels have been scanned without pixel saturation and have been suitably aligned using appropriate image registration software. In the analyses here, the TT900 program (Nonlinear Dynamics) was employed, although any effective image registration program could be used. For optimal performance of this method, any remaining misalignment should be less than the minimum distance between the pinnacles of two adjacent protein spots. There has been no difficulty in aligning the gels in this study, or other gel sets that have been analyzed.

Working on the aligned gels, the Pinnacle method includes of the following steps: (1) Compute the average gel; (2) Denoise the average gel using wavelet shrinkage; (3) Detect pinnacles on the wavelet-denoised average gel; (4) Combine any pinnacles within a specified proximity; (5) Quantify each spot for each gel by taking the maximum intensity within a specified neighborhood of the pinnacle in the average gel; and (6) Apply background correction filters and normalize the spot quantifications.

According to the method, the average gel is used for pinnacle detection. The average gel is constructed by averaging the intensities pixel-by-pixel across all gels in the experiment. Note that this "average gel" differs from the composite gels constructed by PDQuest, Progenesis, and other commercial software that are representations of the spots detected on all of the gels rather than simple pixel-wise averages. It is unnecessary to do any background correction before computing the average gel.

In step 2, wavelet-based denoising filters are applied to denoise the average gel. Over the past ten years, wavelet denoising has become a standard method for removing white noise from signals and images. On these gels, wavelet denoising "smoothes out" small irregularities in the average gel that are consistent with white noise while retaining the larger signals produced by true protein spots. Removal of these irregularities reduces the number of false positive spots detected.

To denoise, the undecimated discrete wavelet transform (UDWT) was used, as implemented in version 2.4 of the Rice Wavelet Toolbox (RWT), which is freely available from their web site (http://www-dsp.rice.edu/software/rwt.shtml). The wavelet denoising consists of the following three steps. First, given a particular choice of wavelet basis, wavelet coefficients are computed for the average gel. These coefficients represent a frequency-location decomposition in both dimensions of the image. The advantage of using the UDWT over the more computationally efficient and commonly used dyadic wavelet transform (DDWT) is that the results are translation-invariant, meaning that the denoising is the same even if you shift or crop the image in either dimension, which results in more effective denoising. We have found the results to be minimally sensitive to choice of wavelet basis; by default we use the Daubechies wavelet with 4 vanishing moments.

Second, hard thresholding is applied to the wavelet coefficients. By hard thresholding, all coefficients are set below a threshold=$\delta\sigma$ to 0, while leaving all coefficients unaffected. The parameter $\sigma$ represents a robust estimator of the standard deviation, following Donoho and Johnstone (1994) by using the median absolute deviation for the highest frequency wavelet coefficients divided by 0.6745, and $\delta$ is a threshold parameter specified by the user, with larger choices of this parameter result in more denoising. In the context of MALDI-MS, values of $\delta$ between 5 and 20 were found to work well (Coombes, et al. 2005). For 2D gels, it has been found that the background white noise is not as strong as MALDI-MS, so smaller values work better. The default value is $\delta=2$.

Third, the denoised signal is reconstructed by applying the inverse UDWT to the thresholded wavelet coefficients. The thresholding works because white noise is equally distributed among all wavelet coefficients, while the signal is focused on a small number of coefficients. Thus, the thresholding zeroes out the large number of wavelet coefficients of small magnitude corresponding mostly to noise, while leaving the small number of coefficients of large magnitude corresponding to signal.

After denoising, spot detection is performed on the wavelet-denoised average gel by detecting all pinnacles. It is determined that a pixel location contains a pinnacle if it is a local maximum in both the horizontal and vertical directions on the gel, and if its intensity was greater than some threshold, by default the 75th percentile on the gel. This leaves us with a list of pixel coordinates marking the pinnacles in the average gel that index the "spots" of interest in the given gel set.

If any pinnacles are found within a given $2k1+1 \times 2k1+1$ square surrounding another pinnacle, then in step 4 these pinnacles are combined by keeping only the one with the highest intensity. This step removes spurious double peaks, and accommodates imperfect alignment, as described in the next step. In our experience, it is rare to see two protein spots with pinnacles less than 5 units from each other, given the resolution of the scanner, which yields a 1024×1024 image of the gel, so by default we use $k1=2$.

Step 5 involves quantifying each spot for each individual gel by taking the maximum intensity within the $2k2+1 \times 2k2+1$ square formed by taking the corresponding pinnacle location in the average gel and extending out $\pm k2$ units in the horizontal and vertical directions on the individual gel. The width $k2$ should be at least as small as the proximity $k1$ in step 5; by default, $k2=k1$. This tolerance enabled us to find the maximum pinnacle intensity for the corresponding spot for each individual gel even when the alignment was not perfect. The accuracy of the alignment only needed to be within $\pm k2$ pixels in both the horizontal and vertical directions.

In the final step, background correction and normalization is performed on the quantifications. If the background appears relatively uniform, subtracting global minimum intensity for the gel works sufficiently well. Whenever the background appears to be spatially varying, a windowed minimum is employed to estimate the background. By using pinnacle intensities rather than spot volumes for quantifications, the background only needs to be estimated for the pixel locations containing pinnacles, so its calculation proceeds very quickly. The default window is +/100 pixels in the horizontal and vertical directions. One must ensure that the window is large enough to extend beyond each spot region to avoid attenuation of the quantified pinnacle intensities.

To normalize, each pinnacle intensity on a given gel is divided by the mean pinnacle intensity for that gel. Note that it is possible to apply a wavelet-based denoising to the individual gels before quantification. While conceptually appealing, this makes little difference in practice, so by default the individual gels are not denoised.

Given N individual gels and p spots, after this step we are left with an N×p matrix of protein expression levels with no missing values. In profiling or group comparison studies, this matrix would be analyzed to find which of the p spots appear to be associated with factors of interest, and worthy of future study.

3.0 Validation Studies

The performance of Pinnacle was compared with current versions of the commercial software packages Progenesis and PDQuest in detecting, matching, and quantifying protein spots using two dilution series, and their performance was compared in differential expression using a group comparison study. The first dilution series was created by Nishihara and Champion (2002), and the second dilution series and the group comparison data was prepared in house. For the dilution series, the percentage of spots correctly matched across gels by the automatic algorithms was summarized. Reliability of spot quantifications was assessed by measuring the strength of linear association ($R^2$) between the spot quantifications and the protein loads in the dilution series for each detected spot. Given the nature of the dilution series, methods yielding more accurate protein quantifications should result in R2 closer to 1. Precision was assessed using the coefficient of variation (% CV) of spots within the different dilution groups. For the group comparison, the number and proportion of spots was summarized with differential expression p-values and local false discovery rates below pre-specified thresholds. All comparisons were based on results generated solely by the three algorithms, without any subsequent editing. In the remainder of this section, detailed descriptions of the data sets were provided, along with the competing algorithms, and the statistical measures used to compare the methods.

3.1 Description of Data Sets
3.1.1 Nishihara and Champion Dilution Series Nishihara and Champion (2002) prepared a dilution series experiment using a sample of E. coli with seven different 2D gel protein loads spanning a 100-fold range (0.5, 7.5, 10, 15, 30, 40, and 50 µg). Four gels were run at each protein load. Details of the conduct of the 2DE are described in Champion, et al. (2001), and the details of the staining and image capture procedures are described in Nishihara and Champion (2002). The images were provided to us courtesy of Dr. Kathleen Champion-Francissen, and were used to compare Pinnacle with PDQuest and Progenesis. Nishihara and Champion previously used this series to evaluate the performance of several 2D analysis packages by analyzing 20 corresponding spots from all the gels. By only investigating 20 spots, however, they did not gain an accurate picture of the methods' performance in detecting, matching, and quantifying spots across the entire gel. Therefore, we evaluated analysis methods using all spots detected in this dilution series. Our Progenesis and PDQuest results for the 20 selected spots were comparable to the results previously obtained by Nishihara and Champion (2002) (data not shown).

3.1.2 SH-SY5Y Neuroblastoma Cell Dilution Series:

SH-SY5Y cells were grown to 60-70% confluence and then harvested. Cells were then resuspended using the ProteoPrep™ (Sigma) total extraction kit and the suspension ultrasonicated on ice for 15 sec. bursts at 70% amplitude for a total time of 1 min. After sonication, the suspension was centrifuged at 15,000×g for 30 min. at 15° C. The samples were then reduced for 1 h at RT by adding tributylphosphine to a final concentration of 5 mM and alkylated in the dark for 1.5 h at RT by adding iodoacetamide to a final concentration of 15 mM. 11 cm IPG strips (Bio-Rad) were then rehydrated in 100 µl of sample buffer for 2 h at RT. Protein samples were then applied to the strips in 150 µl of buffer and IPGs were then focused for 100 kVh. Three replicate gels were run for each of six different protein loads (5 µg, 10 µg, 25 µg. 50 µg, 100 µg, 150 µg). Voltage was increased from 0 to 3000 V over 5 h (slow ramp), 3-10,000 V over 3 h (linear ramp), followed by additional hours at 10,000 V. IPGs were then equilibrated in SDS-equilibration buffer containing 3M urea, 2.5% (w/v) SDS, 50 mM Tris/acetate buffer (pH 7.0), and 0.01% (w/v) bromophenol blue as a tracking dye for 20 min. The equilibrated strips were then placed on 8-16% polyacrylamide gels (Bio-Rad) and proteins separated by size. Run conditions were 50 mA/gel until the bromophenol blue reached the end of the gel. Proteins were visualized using SYPRO ruby stain (Bio-Rad). Gels were fixed for 30 min. in a solution containing 10% methanol and 7% acetic acid. After fixation, gels were stained in 50 ml of SYPRO ruby overnight in the dark. The gels were next destained in 10% methanol and 7% acetic acid for 2 h, and then imaged using a Kodak hnage Station 2000R. Gel images were subsequently cropped to exclude edge artifacts and streaks. The same cropped image area was used for all analytical protocols.

3.1.3 Morphine Group Comparison Data Set

After institutional IACUC approval was obtained, 6 adult male Sprague-Dawley rats were implanted with either morphine 75 mg slow release pellets (National Institute on Drug Abuse) or placebo pellets subcutaneously under isoflurane anesthesia. Tolerance development was monitored daily by tail flick latency (Xu, et al. 2006). After 5 days, animals were sacrificed and spinal cords harvested. The substantia gelatinosa region was then dissected using the transillumination method as previously described (Cuello, et al. 1983). Proteins were extracted from this region and 2D gels run as previously described (Mouledous, et al. 2005).

3.2 Implementation Details for Competing Methods

All gels used in these studies were processed and analyzed using three different methods: Progenesis PG240 version 2006 (Nonlinear Dynamics Ltd., Newcastle-upon-Tyne, UK), PDQuest Version 8.0 (Bio-Rad Laboratories, Hercules, Calif., USA), and the Pinnacle method described in this paper. Pinnacle, as described in Section 2, was applied to images that were first aligned using the TT900 software program (Nonlinear Dynamics), and involved average gel computation, pinnacle detection, and pinnacle-based quantification using computer code written in MATLAB (version R2006a, The MathWorks, Inc.) using Windows XP-based PCs, with default settings used. All procedures were performed in our laboratory. Specific analysis steps are detailed below. Both Progenesis and PDQuest are designed to be run on unaligned gels. In order to ensure that any differences between Pinnacle and these methods are not due solely to the alignment, we also applied these methods to the gel images after they were aligned using TT900.

3.2.1 Progenesis

Gels were processed using the Analysis Wizard, which is a stepwise approach for selecting preprocessing options. Gels were grouped by protein load, and the same gel was selected as the top reference gel for both the aligned and unaligned image sets. Background subtraction was performed using the Progenesis Background method. Combined warping and matching was selected for the unaligned images, and property-based matching was selected for the aligned images, as recommended by the manufacturer. Normalization was not done, since this would eliminate the linearity of quantifications with protein load that we use to evaluate reliability. The minimum spot area was set to 1, and the split factor set at 9. These settings produced a similar number of spots to that reported by Nishihara and Champion using an earlier version of this program (Nishihara and Champion 2002). No manual editing of the data was performed. The data were simply exported to Excel and spots present in 3 of 4 replicates in the Nishihara and Champion series, or 3 of 3 replicates in the SH-SY5Y dilution series determined. Spot volumes of zero were used for spots present on other gels with no match on the current gel.

3.2.2 PDQuest

Gels were processed using the Spot Detection Wizard. Gels were grouped by protein load, default background subtraction and default match settings were applied, and the same master gel was selected for both aligned and unaligned images. This was the same gel used as the top reference gel in Progenesis. We used the "Give Manual Guidance" and "Test Settings" features of the Advanced Spot Detection Wizard. We also used the speckle filter and the vertical and horizontal streak filter in the Advanced Controls, as recommended by the manufacturer. Using these settings we obtained a similar number of spots to that reported by Nishihara and Champion using an earlier version of this program (Nishihara and Champion 2002). Again, we did not normalize spot volumes. No manual editing of the data was performed. The data were exported to Excel and spots present in 3 of 4 replicates in the Nishihara and Champion series, or 3 of 3 replicates in the SH-SY5Y dilution series determined. Spot volumes of zero were used for spots present on other gels with no match on the current gel.

3.3 Statistical Criteria Used for Validation

For each dilution series and method, we summarized the total number of detected spots. For Progenesis and PDQuest results, we computed the number of these that were "unmatched", meaning that they were present on only one gel and not matched to any spot on any other gel. Pinnacle had no unmatched spots since by definition it yielded quantifications for every pinnacle on each gel. We removed all unmatched spots in Progenesis and PDQuest from consideration in the quantitative summaries. We also removed any spots that were not present in at least 3 out of 4 replicate gels for at least one of the protein load groups in the Nishihara and Champion study or 3 out of 3 replicates in the SH-SY5Y cell dilution series. This criterion was used by Nishihara and Champion (2002), and is commonly used by other investigators.

We used the results of the dilution series experiments to assess the matching percentage, reliability, and precision of the different methods' quantifications. The matching percentage for Pinnacle applied to aligned gels was 100%. For PDQuest and Progenesis, we estimated the matching percentage by randomly selecting 10% of the total number of spots that met the above criteria, and then checking by hand the number of times the automatic algorithms correctly matched the corresponding spot on all individual gels for which it was detected to the spot on the reference gel. Note that this measure only deals with matching errors, not detection errors, since gels for which a given spot was not detected at all did not count as a mismatch in terms of the match percentage. Also, incorrect spot splitting (e.g., matching a spot in one gel to the same spot and an adjacent one which were detected as one spot in another gel) was not considered a mismatch in this analysis.

The reliability of quantification for each spot was assessed by computing the coefficient of determination (R2) from a simple linear regression (implemented in Matlab, Mathworks, Inc.) of the mean spot quantification across replicates for each protein load group versus the true protein load. If the correlation (R) was negative, then we set R2=0. The idea driving this analysis was that if the gel ran properly and the quantification method used was robust, then the ratio of quantifications for a given spot for any two gels should be proportional to the ratios of the protein loads on those gels. This measure was computed for all detected spots, not just a select set, so we would get a realistic assessment of the performance of each method across the entire gel. The R2 across all spots within a gel was computed by the mean, five-number summary (5th percentile, Q05, 25th percentile, Q25, the median, Q50, the 75th percentile, Q75, and the 95th percentile, Q95), and by counting the number of "reliable spots." Spots were considered reliable if R2>0.90, which roughly corresponds to a correlation of at least 0.95 between the group mean spot quantifications and the protein load. The number of "reliable spots" gave us a sense of the number of spots that were well quantified by a given method.

The precision of the quantifications was assessed by computing the coefficient of variation (% CV) for each spot detected in the entire gel set across the gels within each protein load group. In the main text, the results are presented from the 30 μg protein load group for the Nishihara and Champion dilution series (as they did in their paper), and in the 50 μg group for the SH-SY5Y dilution series; other results are available in supplementary tables. The % CV across all spots is summarized by the mean and 5 number summary (Q05, Q25, Q50, Q75, Q95), and the number of detected spots were counted with % CV<20. Note that it was not possible to compute CVs for spots with group mean quantifications of zero, so those spots were left out of this analysis.

For the group comparison data, for each method two-sample t-tests were performed with unequal variance assumptions for each detected spot, and summarized the number and proportion of p-values less than 0.001, 0.005, 0.01, and 0.05. The number of spots with q-values<0.10 was summarized. A q-value is a measure of local false discovery rate, and estimates the probability that a given spot is a false positive if called significant (Storey, 2003).

4.0 Results

For the Nishihara and Champion study (NH), Pinnacle detected 1403 spots (FIG. 2), which by definition were found and quantified for all gels. PDQuest detected 2692 spots of which 745 were "unmatched spots" found on only one gel. An additional 571 spots were detected on more than one gel, but not included in the analyses because they were not found on 3 out of 4 gels for at least one group, the same exclusion criterion used by Nishihara and Champion (2002). The match percentage of the 1376 spots found on ¾ gels in at least one group was 60%. Progenesis detected 1986 unique spots, of which 990 were unmatched and 121 not found on ¾ gels in at least one group. The match percentage of the 875 spots found on ¾ gels for at least one group was 84%. If we restricted attention only to those spots that had no missing values on any gel, as we did for Pinnacle, we would have been left with only 377 and 271 spots for PDQuest and Progenesis, respectively. These summaries are shown in Table 9

TABLE 9

Reliability of Quantifications for Detected Spots: Summary of $R^2$ measuring linearity of quantification method across protein loads within dilution series for all spots automatically detected by Pinnacle (Pinn) and for spots meeting the selection criteria below for PDQuest (PDQ) and Progenesis (Prog). Software settings are detailed in the Sections 2 and 3. No manual editing of the datasets was performed. PDQuest and Progenesis were run on the gel sets without alignment, since that is typically how these programs are used. We also ran these programs on the aligned gels (PDQ-a and Prog-a) to verify that the superior performance of Pinnacle was not solely due to image alignment. The summaries include match percentage, number of spots, number of reliable spots, and the mean, median, 5th percentile, 25th percentile, 75th percentile, and 95th percentile for the distribution of $R^2$ across spots. A spot was considered reliable if $R^2 > 0.90$.

| Study | Method | Match Percent | Number of Spots | Reliable Spots ($R^2 > 0.90$) | $R^2$ Mean | Q05 | Q25 | Median | Q75 | Q95 |
|---|---|---|---|---|---|---|---|---|---|---|
| N + C | Pinn | 100% | 1403 | 1203 | 0.924 | 0.613 | 0.951 | 0.978 | 0.990 | 0.995 |
|  | PDQ | 60% | 1376 | 847 | 0.835 | 0.206 | 0.790 | 0.941 | 0.984 | 0.995 |
|  | Prog | 84% | 875 | 666 | 0.883 | 0.253 | 0.909 | 0.973 | 0.990 | 0.996 |

TABLE 9-continued

Reliability of Quantifications for Detected Spots: Summary of $R^2$ measuring linearity of quantification method across protein loads within dilution series for all spots automatically detected by Pinnacle (Pinn) and for spots meeting the selection criteria below for PDQuest (PDQ) and Progenesis (Prog). Software settings are detailed in the Sections 2 and 3. No manual editing of the datasets was performed. PDQuest and Progenesis were run on the gel sets without alignment, since that is typically how these programs are used. We also ran these programs on the aligned gels (PDQ-a and Prog-a) to verify that the superior performance of Pinnacle was not solely due to image alignment. The summaries include match percentage, number of spots, number of reliable spots, and the mean, median, $5^{th}$ percentile, $25^{th}$ percentile, $75^{th}$ percentile, and $95^{th}$ percentile for the distribution of $R^2$ across spots. A spot was considered reliable if $R^2 > 0.90$.

| Study | Method | Match Percent | Number of Spots | Reliable Spots ($R^2 > 0.90$) | $R^2$ Mean | Q05 | Q25 | Median | Q75 | Q95 |
|---|---|---|---|---|---|---|---|---|---|---|
| | PDQ-a | 71% | 1342 | 869 | 0.850 | 0.322 | 0.829 | 0.944 | 0.982 | 0.994 |
| | Prog-a | 80% | 887 | 713 | 0.894 | 0.446 | 0.919 | 0.963 | 0.981 | 0.990 |
| SH-SY5Y | Pinn | 100% | 1162 | 603 | 0.887 | 0.735 | 0.843 | 0.905 | 0.960 | 0.987 |
| | PDQ | 45% | 1297 | 406 | 0.735 | 10.141 | 0.637 | 0.820 | 0.923 | 0.982 |
| | Prog | 30% | 979 | 295 | 0.662 | 0.011 | 0.448 | 0.805 | 0.919 | 0.981 |
| | PDQ-a | 64% | 1103 | 391 | 0.753 | 0.137 | 0.669 | 0.841 | 0.931 | 0.980 |
| | Prog-a | 43% | 1092 | 384 | 0.698 | 0.014 | 0.570 | 0.845 | 0.932 | 0.982 |

*For Progenesis and PDQuest, the number of spots corresponds to the number of spots used in the quantitative analysis, which are those present in at least 3/4 replicate gels within at least 1 of the 7 protein load groups for the Nishihara and Champion study, and at least 3/3 replicate gels within at least 1 of the 6 protein load groups for the SH-SY5Y study.

The top half of Table 1 contains reliability results for the NH study. Pinnacle yielded more reliable spot quantifications over this dilution series (mean R2=0.924) than either PDQuest (0.835) or Progenesis (0.883). Pinnacle found many more reliable spots (defined as R2>0.90) than PDQuest or Progenesis (1203 vs. 847 or 666, respectively). Table 10 shows that Pinnacle also generated more consistent quantifications within the 30 µg protein load group. Pinnacle generated a lower CV (mean 18.4) than either PDQuest (54.7) or Progenesis (40.3), and found far more spots with CV<20% (983 vs. 498 and 304, respectively). The results were similar for the other protein loads.

TABLE 10

Precision of Quantifications for Detected Spots. Summary of coefficient of variation (% CV) for the 30 µg protein load for the Nishihara and Champion study, and the 50 µg load for the SH-SY5Y cell study, for all spots automatically detected by Pinnacle (Pinn) and for spots meeting the selection criteria below for PDQuest (PDQ) and Progenesis (Prog). Software settings are detailed in the Methods. No manual editing of the datasets was performed. PDQuest and Progenesis were run on the gel sets before alignment, since that is typically how these programs are used. We also ran these programs on the aligned gels (PDQ-a and Prog-a) to verify that the superior performance of Pinnacle was not solely due to image alignment. The summaries include the number of spots, plus the mean, median, $5^{th}$ percentile, $25^{th}$ percentile, $75^{th}$ percentile, and $95^{th}$ percentile for the distribution of % CV across spots, and the number of spots with % CV < 20. The % CV results for the other protein load groups are presented in supplementary tables.

| Study | Method | Number of Spots | Number of spots with % CV < 20 | % CV Mean | Q05 | Q25 | Median | Q75 | Q95 |
|---|---|---|---|---|---|---|---|---|---|
| N + C | Pinn | 1403 | 983 | 18.4 | 7.6 | 12.7 | 16.5 | 21.2 | 31.6 |
| | PDQ | 1326 | 498 | 54.7 | 6.5 | 14.4 | 27.5 | 77.5 | 200.0 |
| | Prog | 821 | 1304 | 40.3 | 11.1 | 16.9 | 23.6 | 41.3 | 121.8 |
| | PDQ-a | 1309 | 415 | 55.7 | 9.5 | 17.7 | 29.8 | 76.1 | 200.0 |
| | Prog-a | 852 | 144 | 47.4 | 14.4 | 22.6 | 30.5 | 50.3 | 145.5 |
| SH-SY5Y | Pinn | 1162 | 856 | 15.7 | 3.0 | 7.4 | 12.4 | 20.7 | 40.7 |
| | PDQ | 1166 | 267 | 64.4 | 8.0 | 21.4 | 45.5 | 91.1 | 173.2 |
| | Prog | 787 | 188 | 53.2 | 8.1 | 20.6 | 36.9 | 86.6 | 173.2 |
| | PDQ-a | 1001 | 272 | 58.8 | 7.0 | 19.0 | 38.0 | 88.1 | 173.2 |
| | Prog-a | 931 | 182 | 59.9 | 8.2 | 24.2 | 45.5 | 88.9 | 173.2 |

*The number of spots in this table corresponds to the number of spots from Table 1 for which there was at least one non-missing value for the 30 µg group in the Nishihara and Champion Study, and the 50 µg group in the SH-SY5Y study, since it is not possible to compute CVs for spots with group means of zero.

To determine whether Pinnacle performed better than the other methods only because the gels were pre-aligned, PDQuest and Progenesis were run on the set of aligned gels. In general, we found that the alignment tended to slightly improve the reliability, but not to the levels of Pinnacle (Table 9). Alignment had inconsistent effects on match percentage, and decreased measurement precision for both PDQuest and Progenesis (Table 10).

The last rows of Tables 9 and 10 contain the results from the dilution series created from SH-SY5Y neuroblastoma cell extracts. Pinnacle detected 1013 spots, while PDQuest identified 1297 spots that were found on ⅔ gels in at least one group, with a match percentage of 45%. Progenesis detected 979 spots on ⅔ gels in at least one group with a match percentage of 30%. Pinnacle again yielded more reliable spot quantifications over this dilution series (mean $R^2$=0.887) than either PDQuest (0.735) or Progenesis (0.662), and found many more reliable spots (603) than either PDQuest (406) or Progenesis (295). Again, Pinnacle generated more consistent measurements (mean CV in 50 µg load group 15.7) than either PDQuest (64.4) or Progenesis (53.2), and found far more spots with CV<20% (856 vs. 267 and 188, respectively). Again, it was found that alignment had inconsistent effects on the performance of PDQuest and Progenesis. Reliability and match percentage improved for both methods, but was still far inferior to Pinnacle. Precision improved for PDQuest but worsened for Progenesis.

Table 11 summarizes the results of the group comparison study. Using Pinnacle tended to result in more spots with small p-values. It found a greater number and proportion of spots with p-values less than 0.001, 0.005, 0.01, and 0.05 than Progenesis without alignment or PDQuest with or without alignment. Progenesis with alignment found similar numbers and proportions of spots with p-values less than 0.001, but considerably fewer spots with p-values <0.005, <0.01, or <0.05 than Pinnacle. After adjusting for multiplicities, Pinnacle found considerably more spots with q-values<0.10 than the other methods.

First, image alignment is generally easier and more accurate than one-at-a-time spot matching across a gel series done after spot detection. Image alignment software efficiently uses information from nearby spots on the gel to guide the process. As shown by the validation studies, however, the improvement from Pinnacle is not solely from using the aligned gels images.

Second, as demonstrated in other contexts (Morris, et al. 2005), spot detection using the average gel is not just quicker, but should result in greater sensitivity and specificity compared with spot detection on individual gels. This is because features corresponding to true protein spots will tend to be present on many gels and thus will be reinforced in the average gel, while artifacts and noise will tend to average out. The central limit theorem suggests that the noise level in the average gel will be less than the noise level in an individual gel by a factor of $\sqrt{N}$, and thus, it becomes easier to see the protein signal. Thus, the arithmetic average gel should have greater sensitivity for peak detection than individual gels for any proteins present in at least $1/\sqrt{N}$ of the gels. By this principle, we should be able to more reliably detect fainter spots, thus improving the realized dynamic range of the 2D gel analysis. This also suggests that sensitivity, specificity and spot detection should improve, not deteriorate, as more gels are included. This is in marked contrast to standard methods that detect spots on individual gels, since in that setting, the occurrence of missing spots and matching errors tend to increase with larger gel sets.

Third, accurate pinnacle detection is aided by the wavelet denoising that adaptively removes noise without severely attenuating the true protein spots. In recent years, wavelet denoising has become a standard tool in nearly every area of signal processing, so is a natural tool to use in denoising 2DE images.

Fourth, the use of pinnacles instead of spot boundaries to define and quantify spots greatly reduces computational complexity, and decreases the variability of spot quantifications. Provided the gel images are not saturated, protein spots typi-

TABLE 11

Comparison of Methods for Morphine Group Comparison Dataset. Summary of number of detected spots, and number (%) of spots with p-values less than 0.001, 0.005, 0.01, and 0.05 for morphine group comparison data set, for the different preprocessing methods.

| | | | | p-values | | | |
| --- | --- | --- | --- | --- | --- | --- | --- |
| | Method | Number of Spots | q-val < 0.10 | <0.001 | <0.005 | <0.01 | <0.05 |
| Morphine | Pinn | 1687 | 308 | 6 (0.4%) | 40 (2.4%) | 80 (4.7%) | 330 (19.5%) |
| group | PDQ | 992 | 2 | 3 (0.3%) | 11 (1.1%) | 22 (2.2%) | 94 (9.5%) |
| comparison | Prog | 864 | 0 | 1 (0.1%) | 9 (1.0%) | 17 (2.0%) | 84 (9.7%) |
| | PDQ-a | 930 | 2 | 2 (0.2%) | 13 (1.4%) | 24 (2.6%) | 89 (9.6%) |
| | Prog-a | 972 | 32 | 8 (0.8%) | 18 (2.1%) | 31 (3.5%) | 126 (14.4%) |

5.0 Discussion

A new method for detecting and quantifying protein spots on 2DE gel sets has been described and validated. Designed for aligned gel images, it is automatic, fast, and yields reliable results without any need for hand editing. The results demonstrated that quantifications using Pinnacle are more reliable and precise than two currently popular analysis methods, yielding many more reliable spots, and having no missing data issue. It runs very quickly, taking just 56.6, 32.9, and 29.7 seconds, respectively, for the data sets considered in this paper Pinnacle is considerably simpler than methods like Progenesis and PDQuest, and this simplicity is the key not just to its speed but also its superior performance. There are several factors contributing to this effect.

cally appear as mountain-like structures with well-defined pinnacles. It is quicker and easier to detect these pinnacles than to detect spots using more complex algorithms. Also, unlike spot boundaries, pinnacles are consistent and well defined even when spots overlap. The reduced variability comes from the fact it is not necessary to detect spot boundaries, a difficult and error-prone exercise.

It has long been assumed that spot volumes should correspond to true protein abundance, so we were initially surprised to find that the pinnacle-based method resulted in more reliable and precise quantifications than volume-based, methods. However, the pinnacle intensity should be strongly correlated with the spot volume when a given spot has a common shape across gels. The empirical investigations suggest that this assumption holds in practice for the vast majority spots on gels. Mahon and Dupree (2001) have similarly observed that pinnacle intensities are linearly related to spot volumes. The studies indicate that our pinnacle-based method results in considerably smaller CVs than conventional spot volume-based analysis methods, which in profiling studies would result in greater statistical power for detecting differentially expressed proteins, as in our group comparison results. Also, Pinnacle's unambiguous spot definition on all gels results in no missing data, which is another factor in increasing quantitative precision.

6.0 Conclusion

The lack of efficient, effective, and reliable methods for 2D gel analysis has been a major factor limiting the contribution of 2DE to biomedical research. Currently, gel analysis is extremely time consuming and subjective, and it is difficult to conduct the larger studies required to have adequate statistical power for detecting proteins differentially expressed across experimental conditions. Ineffective preprocessing leads to reduced numbers of accurately detected and matched spots and unreliable, imprecise quantifications. This can cause investigators to miss potentially important discoveries that could be made from their data. The Pinnacle method is automatic, quick, robust, precise, and without potential biases that could be introduced by manual editing. It tends to perform better, not worse, in larger studies, so is well-suited for the larger studies now being conducted. This simple, yet novel method has the potential to help maximize the impact of 2DE on biological research, and also has the potential to be applied to perform spot detection and quantification in other settings where image data with spots are encountered, including DIGE and LC-MS.

The above description is given by way of example, and not limitation. Given the above disclosure, one skilled in the art could devise variations that are within the scope and spirit of the invention disclosed herein. Further, the various features of the embodiments disclosed herein can be used alone, or in varying combinations with each other and are not intended to be limited to the specific combination described herein. Thus, the scope of the claims is not to be limited by the illustrated embodiments.

While various embodiments of the present invention have been described above, it should be understood that they have been presented by way of example only, and not of limitation. Likewise, the various diagrams may depict an example architectural or other configuration for the invention, which is done to aid in understanding the features and functionality that can be included in the invention. The invention is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the present invention. In addition, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the invention is described above in terms of various exemplary embodiments and implementations, it should be understood that the various features, aspects and functionality described in one or more of the individual embodiments are not limited in their applicability to the particular embodiment with which they are described. These example embodiments may instead be applied, alone or in various combinations, to one or more of the other embodiments of the invention. This is true whether or not such embodiments are described and whether or not such features are presented as being a part of a described embodiment. Thus, the breadth and scope of the present invention should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more," or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

A group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although items, elements or components of the invention may be described or claimed in the singular, the plural is contemplated to be within the scope thereof unless limitation to the singular is explicitly stated.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed across multiple locations. Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

What is claimed is:

1. A method for detecting and quantifying protein spots in a plurality of two-dimensional electrophoresis gel images that have been aligned to one another, each gel image having a two-dimensional array of pixels, the method comprising:

a processor to implement;
a) generating an average gel image by taking a pixel-by-pixel average of the intensities of individual gel images, as aligned to one another;
b) detecting spots on the average gel image using pinnacle detection, each detected spot of the average gel image having a pinnacle and a pinnacle location; and
c) quantifying spots on one or more of the individual gel images using maximum intensities within fixed neighborhoods surrounding pinnacle locations found in the average gel image;
wherein, further comprising the step of baseline correcting the individual gel images before generating an average gel image.

2. The method according to claim 1, wherein pinnacle detection comprises applying a wavelet-based de-noising filter on the average gel image and then detecting pixels whose intensities are local maxima in both the vertical and horizontal directions and are above a specific threshold.

3. The method according to claim 2, wherein the application of the wavelet-based de-noising filter comprises:
a) generating wavelet coefficients for a discrete wavelet transform of the average gel image given a particular choice of wavelet basis;
b) applying hard thresholding to the wavelet coefficients; and
c) generating a de-noised average gel image by applying an inverse discrete wavelet transform to the thresholded wavelet coefficients.

4. The method of claim 3 wherein the discrete wavelet transform comprises an undecimated discrete wavelet transform, and wherein the inverse discrete wavelet transform comprises an inverse undecimated discrete wavelet transform.

5. The method according to claim 2, wherein the specific threshold intensity is an intensity equal to or greater than the $75^{th}$ percentile on the average gel image.

6. The method according to claim 1, wherein the method further comprises combining spots with pinnacles within +/−2 pixels between steps (b) and step (c).

7. The method according to claim 1, wherein, prior to performing step (a), the individual gel images are baseline corrected by subtracting the global minimum pixel intensity on each gel image from every pixel on the individual gel image.

8. A computer program product stored on a computer readable medium for directing a computer processor to detect and quantify protein spots in a plurality of two-dimensional gel electrophoresis images that have been aligned to one another, each gel image having a two-dimensional array of pixels, the computer program product comprising:
a computer readable medium;
an initial set of instructions embodied on the computer readable medium adapted to direct a data processor to receive data representative of the plurality of two-dimensional gel electrophoresis images;
a first set of instructions embodied on the computer readable medium adapted to direct the data processor to generate an average gel image by taking a pixel-by-pixel average of the intensities of the individual gel images, as aligned to one another;
a second set of instructions embodied on the computer readable medium adapted to direct the data processor to detect spots on the average gel image by detecting pinnacles, each detected spot of the average gel image having a corresponding pinnacle and pinnacle location;
a third set of instructions embodied on the computer readable medium adapted to direct the data processor to quantify spots on one or more of the individual gel images using maximum intensities within fixed neighborhoods surrounding pinnacle locations found in the average gel image;
wherein, further comprising an additional set of instructions embodied on the computer readable medium that, prior to the generation of the average gel image, directs the data processor to subtract the global minimum pixel intensity of each individual gel image from every pixel intensity of the gel image.

9. The computer program product according to claim 8, further comprising an additional set of instructions embodied on the computer readable medium that, prior to the detection of spots on the average gel image, directs the data processor to apply a wavelet-based de-noising filter to the average gel image to generate a de-noised average gel image, the additional set of instructions comprising:
instructions that direct the data processor to generate wavelet coefficients of a discrete wavelet transform for the average gel image given a particular choice of wavelet basis;
instructions that direct the data processor to apply hard thresholding to the wavelet coefficients by setting all coefficients with magnitudes below a threshold $\phi=\delta\sigma$ to 0 while leaving all coefficients with magnitudes $\geq \phi$ unaffected;
instructions adapted to direct the data processor to generate the de-noised average gel image by applying an inverse discrete wavelet transform to the thresholded wavelet coefficients.

10. The computer program product according to claim 8, wherein the second set of instructions directs the data processor to detect a pinnacle as pixel location whose intensity is a local maximum in both the horizontal and vertical directions on the average gel image, and whose intensity is greater than a threshold, by default the $75^{th}$ percentile intensity value of the average gel image.

11. The computer program product according to claim 8, further comprising an additional set of instructions embodied on the computer readable medium that, prior to the quantification of spots on each individual gel image, direct the data processor to combine pinnacles that are within a predetermined proximity, and keeping the one with the highest intensity.

12. A computer program stored on a computer readable medium for controlling the computer to perform a process for detecting and quantifying protein spots in 2-dimensional gel electrophoresis data, the process comprising:
a) receiving data related to superimposition of corresponding gel features across gels;
b) generating an average gel by taking a pixel-by-pixel average of aligned gel intensities;
c) detecting spots on the average gel by applying a wavelet-based de-noising filter and then detecting pinnacles;
d) quantifying spots on each individual gel using the maximum intensity within fixed neighborhoods surrounding the pinnacle locations found in the average gel;
wherein, further comprising, between step (a) and step (b), the step of subtracting the global minimum pixel intensity on each gel from every pixel on the gel.

13. The computer program according to claim 12, wherein applying the wavelet-based de-noising filter in step (c) comprises the steps of:
computing wavelet coefficients for the average gel given a particular choice of wavelet basis;

applying hard thresholding to the wavelet coefficients by setting all coefficients with magnitude below a threshold $\phi=\delta\sigma$ to 0 while leaving all coefficients with magnitude$\geq\phi$ unaffected;

reconstructing the de-noised signal by applying the inverse UDWT to the threshold wavelet coefficients.

14. The computer program according to claim 12, wherein detecting the pinnacles in step (c) comprises detecting each pixel location that is a local maximum in both the horizontal and vertical directions on a gel wherein its intensity is greater than a predetermined threshold.

15. The computer program according to claim 12, further comprising, between step (c) and step (d), the step of combining pinnacles that are within a predetermined proximity, and keeping the one with the highest intensity.

* * * * *